US 9,116,126 B2

United States Patent
Hassan et al.

(10) Patent No.: US 9,116,126 B2
(45) Date of Patent: Aug. 25, 2015

(54) TECHNIQUES FOR REMOVING A CONTAMINANT LAYER FROM A THERMAL BARRIER COATING AND ESTIMATING REMAINING LIFE OF THE COATING

(75) Inventors: Waled T. Hassan, Indianapolis, IN (US);
William J. Brindley, Hebron, CT (US);
Eric H. Jordan, Storrs, CT (US);
Michael W. Renfro, Manchester, CT (US)

(73) Assignees: Rolls-Royce Corporation, Indianapolis, IN (US); The University of Connecticut, Farmington, CT (US)

( * ) Notice: Subject to any disclaimer, the term of this patent is extended or adjusted under 35 U.S.C. 154(b) by 538 days.

(21) Appl. No.: 13/509,971

(22) PCT Filed: Nov. 16, 2010

(86) PCT No.: PCT/US2010/056791
§ 371 (c)(1),
(2), (4) Date: Sep. 14, 2012

(87) PCT Pub. No.: WO2011/060404
PCT Pub. Date: May 19, 2011

(65) Prior Publication Data
US 2013/0062323 A1 Mar. 14, 2013

Related U.S. Application Data

(60) Provisional application No. 61/261,633, filed on Nov. 16, 2009.

(51) Int. Cl.
*G01J 3/30* (2006.01)
*G01N 21/71* (2006.01)

(52) U.S. Cl.
CPC .................................. *G01N 21/718* (2013.01)

(58) Field of Classification Search
USPC .................................................. 356/300–334
See application file for complete search history.

(56) References Cited

U.S. PATENT DOCUMENTS 5,798,832 A      8/1998   Hnilica et al.
6,008,896 A  *  12/1999   Sabsabi et al. ................ 356/318
(Continued)

FOREIGN PATENT DOCUMENTS

DE       102004051311 A1    8/2006
EP            0863396 A3    9/1998

OTHER PUBLICATIONS

Das et al., "Detection of a marker layer in a 7YSZ thermal barrier coating by femtosecond laser-induced breakdown spectroscopy", Surface & Coatings Technology 202, 2008, pp. 3940-3946.
(Continued)

*Primary Examiner* — Abdullahi Nur
(74) *Attorney, Agent, or Firm* — Shumaker & Sieffert, P.A.

(57) ABSTRACT

Systems and techniques are disclosed for removing contaminants from a surface of a thermal barrier coating (TBC) and, optionally, estimating the remaining lifetime of the TBC. Laser induced breakdown spectroscopy (LIBS) is one method that may be used to remove contaminants from a surface the TBC prior to performing photo luminescence piezo spectroscopy (PLPS) or another spectroscopic technique on a thermally grown oxide (TGO). LIBS may facilitate monitoring substantially in real-time the chemical composition of the material removed. LIBS may be used to remove substantially only the contaminants with minimal effects on the underlying TBC. One technique for determining when to stop removal of material from the TBC is cross-correlation between a spectrum collected from the ablated material and a reference spectrum collected from a reference substrate. In some embodiments, the same system may be used to perform LIBS to remove impurities and PLPS to measure stress in the TGO.

30 Claims, 9 Drawing Sheets

(56) References Cited

U.S. PATENT DOCUMENTS

| | | | |
|---|---|---|---|
| 7,535,565 | B1 | 5/2009 | Viertl et al. |
| 2005/0167405 | A1 | 8/2005 | Stoltz et al. |
| 2007/0296966 | A1 | 12/2007 | Benicewicz et al. |

OTHER PUBLICATIONS

Das et al., "Depth-profiling study of a thermal barrier coated superalloy using femtosecond laser-induced breakdown spectroscopy", Spectrochimica Acta Part B, vol. 63, 2008, pp. 27-36.

Tong et al., "Real-time control of ultrafast laser micromachining by laser-induced breakdown spectroscopy", Applied Optics, Mar. 20, 2004, vol. 43, No. 9, 10 pages.

Notification of Transmittal of the International Search Report and PCT Written Opinion, or the Declaration from corresponding PCT Application No. PCT/US2010/056791, mailed Mar. 18, 2011. (14 pages).

Notification Concerning Transmittal of International Preliminary Report on Patentability (Chapter I of the Patent Cooperation Treaty) from corresponding PCT Application No. PCT/US2010/056791, mailed May 31, 2012, (9 pages).

Response to Office Action dated Feb. 27, 2014, from counterpart Canadian Application No. 2,781,104, filed Aug. 27, 2014, 22 pp.

Office Action from Canadian counterpart application No. 2,781,104 dated Feb. 27, 2014, 2 pp.

* cited by examiner

TECHNIQUES FOR REMOVING A CONTAMINANT LAYER FROM A THERMAL BARRIER COATING AND ESTIMATING REMAINING LIFE OF THE COATING

CROSS REFERENCE TO RELATED APPLICATIONS

This application claims the benefit of U.S. Provisional Application No. 61/261,633, filed Nov. 16, 2009, which is incorporated herein by reference in its entirety.

TECHNICAL FIELD

The disclosure is directed to techniques for cleaning an article comprising a thermal barrier coating and, optionally, estimating remaining life of the thermal barrier coating.

BACKGROUND

The components of high-temperature mechanical systems, such as, for example, gas-turbine engines, must operate in severe environments. For example, the high-pressure turbine blades and vanes exposed to hot gases in commercial aeronautical engines typically experience metal surface temperatures of about 1000° C., with short-term peaks as high as 1100° C.

Typical components of high-temperature mechanical systems include a Ni- or Co-based superalloy substrate. The substrate can be coated with a thermal barrier coating (TBC) to reduce substrate surface temperatures. The thermal barrier coating may include a thermally insulative ceramic topcoat, and may be bonded to the substrate by an underlying metallic bond coat.

The component may be exposed to widely different temperatures, e.g., up to 1100° C. during operation and on the order of 25° C. when operation is ceased. These widely different temperatures may cause significant stress at the interface of the bond coat and thermally insulative ceramic topcoat, which eventually may lead to spallation of the TBC from the substrate. The stress may be due to, for example, oxidation of the bond coat and/or the bond coat and thermally insulative ceramic topcoat having different coefficients of thermal expansion. In order to improve maintenance of the high-temperature mechanical systems, it may be desirable to estimate when the TBC is expected to fail and should be repaired or the component be replaced.

SUMMARY

In general, the present disclosure is directed to systems and techniques for determining whether a portion of an article includes a component of a thermal barrier coating (TBC) and, optionally, estimating the remaining lifetime of the TBC. In some embodiments, the systems and techniques described herein also are useful for removing a portion of a contaminant layer from a surface of the TBC. The systems and techniques described herein may remove the portion of the contaminant layer from the surface of the TBC while reducing or minimizing removal of material from the TBC. Laser induced breakdown spectroscopy (LIBS) is one technique that may be used to determine whether a portion of an article includes a component of a thermal barrier coating and, optionally, to remove contaminants from a surface of the TBC prior to performing photo luminescence piezo spectroscopy (PLPS) or another optical technique on the thermally grown oxide (TGO) of the article. One advantage of utilizing LIBS is that the chemical composition of the removed material may be monitored in real-time (e.g., as material is ablated from the surface). Therefore, LIBS may be used to remove substantially only portions of material including the contaminants with minimal effects on the underlying TBC. Additionally, in some embodiments, the same system may be used to perform LIBS to determine whether a portion of an article includes a component of a thermal barrier coating and, if necessary, remove impurities, and subsequently to perform PLPS to measure stress in the TGO.

In one aspect, the disclosure is directed to a method that includes exposing a portion of an article comprising a thermal barrier coating (TBC) to sufficient electromagnetic energy to ablate the portion of the article. According to this aspect of the disclosure, the portion of the article comprises the TBC. The method further includes collecting a spectrum of electromagnetic energy emitted by the portion of the article after ablation, and determining, based on the collected spectrum of electromagnetic energy, that a component of the TBC is present in the portion of the article.

In another aspect, the disclosure is directed to a computer-readable medium that includes instructions that cause a processor to control an energy source to expose a portion of an article comprising a thermal barrier coating (TBC) to sufficient electromagnetic energy to ablate the portion of the article. According to this aspect of the disclosure, the portion of the article comprises the TBC. Additionally, the computer-readable medium includes instructions that cause the processor to collect a spectrum of electromagnetic energy emitted by the portion of the article after ablation, and determine, based on the collected spectrum of electromagnetic energy, that a component of the TBC is present in the portion of the article.

In another aspect, the disclosure is directed to a method that includes outputting electromagnetic energy at a first energy setting from an energy source, and exposing a portion of an article comprising a substrate, a thermal barrier coating comprising a thermally grown oxide on the substrate, and a thermally insulative layer on the thermally grown oxide to the first energy setting to ablate the portion of the article. According to this aspect of the disclosure, the portion of the article comprises a portion of the thermally insulative layer. The method also includes collecting a spectrum of electromagnetic energy emitted by the portion of the article after ablation, and determining, based on the collected spectrum of electromagnetic energy, that a component of the thermally insulative layer is present in the portion of the article. According to this aspect of the disclosure, the method further includes outputting electromagnetic energy at a second energy setting from the energy source, where the second energy setting is different than the first energy setting, exposing a portion of the thermally grown oxide to the second energy setting, detecting electromagnetic energy fluoresced by the portion of the thermally grown oxide in response to exposure to the second energy setting, and estimating a remaining life of the thermal barrier coating based on the electromagnetic energy fluoresced by the portion of the thermally grown oxide.

In a further aspect, the disclosure is directed to a system that includes an energy source configured to output electromagnetic energy at a first energy setting to ablate a portion of a thermal barrier coating present on an article and at a second energy setting to induce fluorescence in a thermally grown oxide layer on the article. According to this aspect of the disclosure, the system also includes a spectrometer configured to receive emitted electromagnetic energy emitted by the portion of the thermal barrier coating and fluoresced electromagnetic energy fluoresced by the thermally grown oxide layer, and a control unit configured to control operation of the energy source and estimate a remaining life of the thermal barrier coating based on the fluoresced electromagnetic energy.

In an additional aspect, the disclosure is directed to a computer-readable medium that includes instructions that cause a processor to control an energy source to output electromagnetic energy at a first energy setting to expose to the first energy setting a portion of an article comprising a substrate, a thermal barrier coating comprising a thermally grown oxide on the substrate, and a thermally insulative layer on the thermally grown oxide to ablate the portion of the article. According to this aspect of the disclosure, the portion of the article comprises a portion of the thermally insulative layer. Additionally, the computer-readable medium comprises instructions that cause the processor to collect a spectrum of electromagnetic energy emitted by the portion of the article after ablation and determine, based on the collected spectrum of electromagnetic energy, that a component of the thermally insulative layer is present in the portion of the article. This aspect of the disclosure further requires that the computer-readable medium comprises instructions that cause the processor to control the energy source to output electromagnetic energy at a second energy setting to expose a portion of the thermally grown oxide to the second energy setting, where the second energy setting is different than the first energy setting. Further, the computer-readable medium comprises instructions that cause the processor to detect electromagnetic energy fluoresced by the portion of the thermally grown oxide in response to exposure to the second energy setting and estimate a remaining life of the thermal barrier coating based on the electromagnetic energy fluoresced by the portion of the thermally grown oxide.

In another aspect, the disclosure is directed to a laser-induced breakdown spectroscopy system that includes a control unit that collects a reference spectrum from a reference substrate and collects a sample spectrum from an article comprising a substrate, a thermal barrier coating comprising a thermally grown oxide on the substrate, and a thermally insulative layer on the thermally grown oxide to ablate a portion of the article. According to this aspect of the disclosure the control unit cross-correlates the reference spectrum and the sample spectrum to determine a cross-correlation value and determines whether to stop ablation of the article based on the cross-correlation value.

In a further aspect, the disclosure is directed to a method that includes collecting a reference spectrum from a reference substrate and collecting a sample spectrum from an article comprising a substrate, a thermal barrier coating comprising a thermally grown oxide on the substrate, and a thermally insulative layer on the thermally grown oxide to ablate a portion of the article. According to this aspect of the disclosure, the method further includes cross-correlating the reference spectrum and the sample spectrum to determine a cross-correlation value and determining whether to stop ablation of the article based on the cross-correlation value.

In an additional aspect, the disclosure is directed to a computer-readable medium that includes instructions that cause a processor to collect a reference spectrum from a reference substrate and collect a sample spectrum from an article comprising a substrate, a thermal barrier coating comprising a thermally grown oxide on the substrate, and a thermally insulative layer on the thermally grown oxide to ablate a portion of the article. According to this aspect of the disclosure, the computer-readable medium comprises further instructions that cause the processor to cross-correlate the reference spectrum and the sample spectrum to determine a cross-correlation value and determine whether to stop ablation of the article based on the cross-correlation value.

DETAILED DESCRIPTION

Figure 1A:
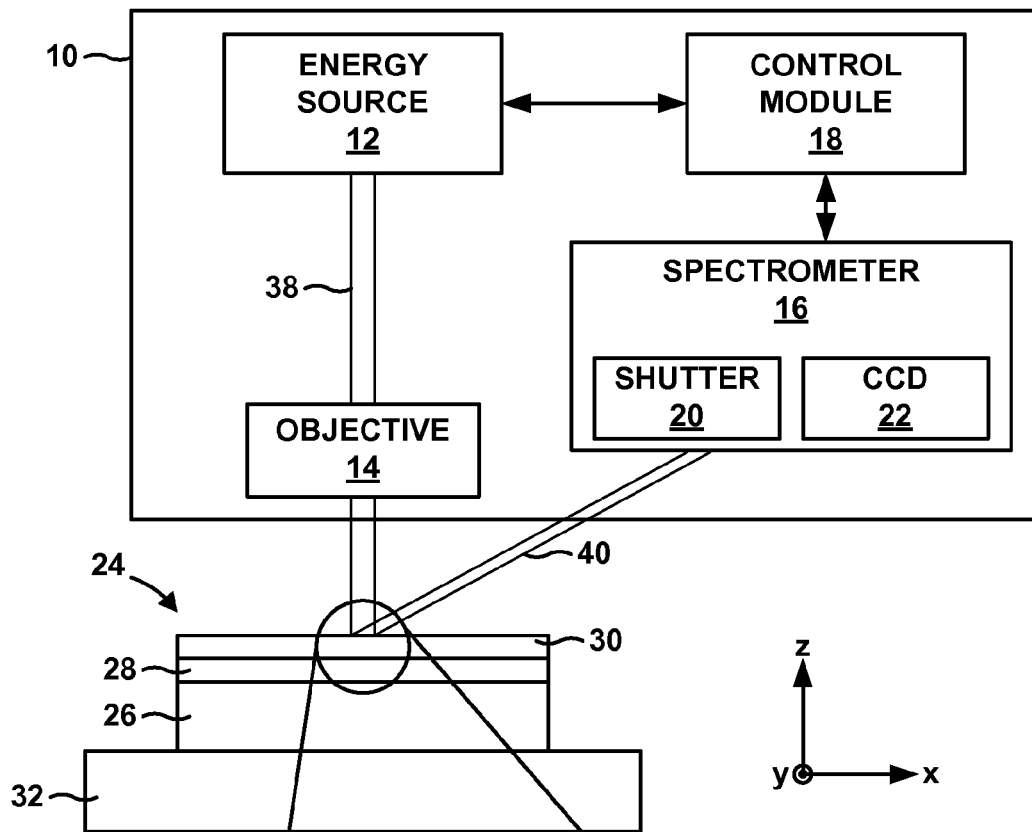
FIGS. 1A and 1B are conceptual diagrams of an exemplary system for determining whether a portion of an article includes a component of a thermal barrier coating (TBC) and, if a contaminant layer is present on the TBC, removing a portion of the contaminant layer from the TBC.

In general, the present disclosure is directed to systems and techniques for determining whether a portion of an article includes a component of a thermal barrier coating (TBC) in a controlled and monitored fashion and, optionally, estimating the remaining lifetime of the TBC. In some embodiments, the systems and techniques described herein also are useful for removing a portion of a contaminant layer from a surface of the TBC. One technique that may be used to estimate the remaining life of an uncontaminated TBC applied to a substrate is Photo Luminescence Piezo Spectroscopy (PLPS). PLPS is a nondestructive technique that uses laser light to excite fluorescence in $Cr^{3+}$ ions present in an alumina ($Al_2O_3$) thermally grown oxide (TGO) layer. The $Cr^{3+}$ ions fluoresce at two distinct peaks. Mechanical stresses in the TGO may cause deformation in the crystal structure of the $Cr^{3+}:Al_2O_3$, which may cause the wavelengths of the $Cr^{3+}$ fluorescence peaks to shift. A relationship between the stress in the TGO, as indicated by the shift of the fluorescence peak, and the remaining life of the TBC may be developed and can be used to estimate the remaining life of the TBC.

PLPS relies on the assumption that the TBC is transparent to the laser used in the PLPS measurement and the only source of fluorescence is in the TGO. However, during use of an article coated with a TBC, such as a gas turbine engine blade, contaminants may accumulate on a surface of the TBC. These contaminants may not be transparent to the laser used in PLPS. In particular, the contaminants may fluoresce at wavelengths similar to the $Cr^{3+}$ in the TGO, scatter the electromagnetic energy from the laser, absorb the electromagnetic energy from the laser, or in some other way prevent sufficient energy from reaching the TGO, which may obscure the peaks of interest in the PLPS spectra. Because of this, it may be important to determine whether a portion of the TBC includes contaminants or a contaminant layer on a surface of the TBC, and if contaminants are present, to remove the contaminants from the surface of the TBC prior to performing the PLPS measurement. In particular, removal of the contaminants that does not significantly harm the TBC and underlying article is desired, so that the article can continue use after estimation of the remaining life.

The inventors have discovered that laser induced breakdown spectroscopy (LIBS) is one non-destructive method that may be used to determine whether a portion of the TBC includes contaminants or a contaminant layer on a surface of the TBC, and if contaminants are present, to remove contaminants from a surface of an article coated with a TBC prior to performing PLPS or another optical technique, such as, for example, optical coherence tomography, on the TGO of the article. LIBS allows real-time monitoring of the chemical composition of the removed material (e.g., monitoring as material is ablated from the surface). Therefore, LIBS may be used to remove substantially only portions of material that include contaminants, with minimal effects on the underlying TBC. Additionally, in some embodiments, the same system may be used to perform LIBS to determine whether a portion of an article includes a component of a thermal barrier coating and, if necessary, remove impurities, prior to, performing PLPS to measure stress in the TGO.

One technique of determining when to stop the LIBS ablation process (e.g., determining whether the portion of the article includes the component of the thermal barrier coating or a component of the contaminant layer) is cross-correlation. In the context of this disclosure, cross-correlation includes the comparison of an electromagnetic energy spectrum collected from an article including a TBC and a contaminant layer to a reference electromagnetic energy spectrum collected from a non-contaminated reference substrate including a chemical composition substantially similar to that of the TBC. Cross-correlation compares the content of the respective spectra and calculates a single value representative of the similarity or dissimilarity of the spectra. By calculating cross-correlation values for sequential ablations of the article including the TBC and comparing the calculated cross-correlation values to previously calculated cross-correlation values for the same article, the determination of when to stop the LIBS ablation process may be made automatically (e.g., without user intervention). In some embodiments, cross-correlation may be advantageous because it may be self-calibrating and correct for any day-to-day or session-to-session variability in devices or systems used to perform LIBS, as will be described below.

Figure 1B:
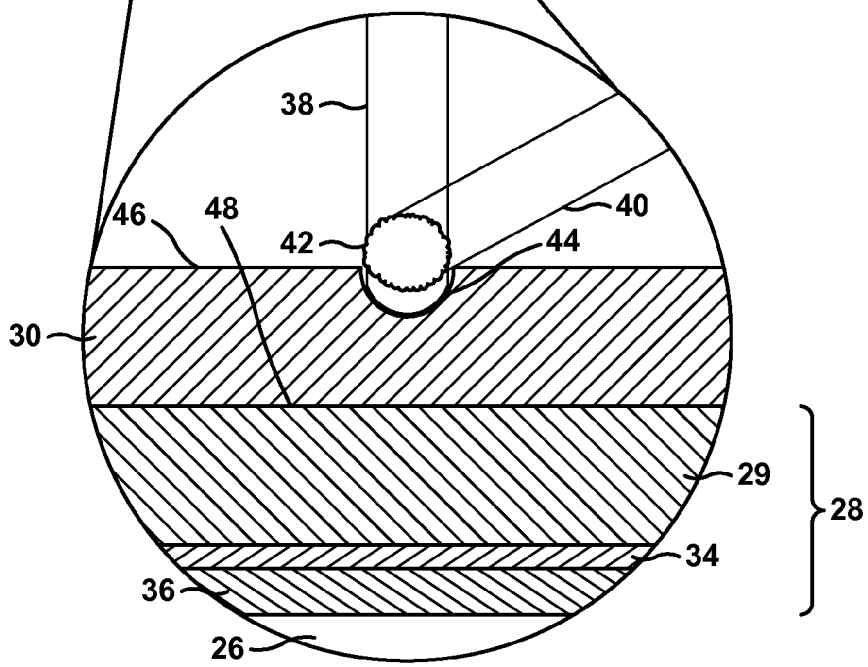

FIGS. 1A and 1B are conceptual diagrams of an exemplary LIBS system 10 for determining whether a portion of an article includes a component of a thermal barrier coating and, if a component of a contaminant layer is present in the portion, removing a portion of a contaminant layer 30 from an article 24 coated with a TBC 28. LIBS system 10 may include an energy source 12, a focusing lens (or objective lens) 14, a spectrometer 16, a control unit 18, and a stage 32 to which article 24 is coupled. FIG. 1B is a cross-sectional diagram that shows further detail of the TBC 28, contaminant layer 30, a beam of electromagnetic energy 38, and emitted electromagnetic energy 40.

Article 24 includes a substrate 26 and TBC 28 formed on substrate 26. As shown in FIG. 1B, TBC 28 may include a bond coat 36 formed on substrate 26, a thermally grown oxide (TGO) 34 formed on bond coat 36, and a thermally insulative layer 29 formed on TGO 34. Article 24 may be a component of a high temperature mechanical system, such as, for example, a gas turbine engine. For example, article 24 may be a turbine blade, a turbine disk, a blade shroud, a combustor liner, a flame holder, or the like.

Substrate 26 may comprise, for example, a superalloy, such as a superalloy based on Ni, Co, Ni/Fe, and the like. A substrate 26 including a superalloy may include other additive elements to alter its mechanical properties, such as toughness, hardness, temperature stability, corrosion resistance, oxidation resistance, and the like, as is well known in the art. In some embodiments, substrate 26 may include at least one of Cr, Mo, Ta, B, C, Co, Al, Hf, Re, or the like. Any useful superalloy may be utilized for substrate 26, including, for example, those available from Martin-Marietta Corp., Bethesda, Md., under the trade designation MAR-M247; those available from Cannon-Muskegon Corp., Muskegon, Mich., under the trade designations CMSX-4 and CMXS-10; those available from Haynes International, Kokomo, Ind., under the trade designations Haynes 230® and Hastelloy X®; and the like.

Bond coat 36 may be formed on substrate 26, and may increase adhesion between substrate 26 and thermally insulative layer 29. Bond coat 36 may include an alloy, such as a MCrAlY alloy (where M is Ni, Co, or NiCo), a β-NiAl nickel aluminide alloy (either unmodified or modified by Pt, Cr, Hf, Zr, Y, Si, and combinations thereof), a γ-Ni+γ'-Ni$_3$Al nickel aluminide alloy (either unmodified or modified by Pt, Cr, Hf, Zr, Y, Si, and combinations thereof), or the like.

Bond coat 36 may be selected based on a number of considerations, including the chemical composition and phase constitution of thermally insulative layer 29 and substrate 26. For example, when substrate 26 includes a superalloy with a γ-Ni+γ'-Ni$_3$Al phase constitution, bond coat 36 may include a γ-Ni+Ni$_3$Al phase constitution to better match the coefficient of thermal expansion of substrate 26, and therefore increase the mechanical stability (adhesion) of bond coat 36 to substrate 26.

Bond coat 36 may be formed on substrate by, for example, chemical vapor deposition (CVD), pack cementation, above-the-pack deposition, slurry coating, sputtering, cathodic arc deposition, electron beam evaporation, plasma deposition, or the like.

While not shown in FIGS. 1A and 1B, in some embodiments, article 24 may not include a bond coat 36. For example, TGO 34 may be formed directly on substrate 26.

TGO 34 may be formed by oxidizing bond coat 36. For example, bond coat 36 may be heated in an oxidizing atmosphere to grow TGO 34 on bond coat 36. In other embodiments, TGO 34 may be deposited on bond coat 36 (or substrate 26) by chemical vapor deposition or another suitable deposition technique. In many embodiments, TGO 34 may comprise alumina ($Al_2O_3$), along with other elements diffused from bond coat 36 or substrate 26. For example, TGO 34 may include Cr or Cr ions. The other elements in TGO 34 may diffuse during the heat treatment that forms TGO 34 or during chemical vapor deposition of TGO 34.

Thermally insulative layer 29 may provide thermal protection (insulation) and/or chemical protection to substrate 26. Thermally insulative layer 29 may include, for example, yttria-stabilized zirconia, yttria-stabilized hafnia, rare earth oxides, aluminates, silicates, zirconates, a rare earth oxide-stabilized zirconia, a rare earth oxide-stabilized hafnia, or combinations thereof. In some embodiments, thermally insulative layer 29 may be formed as a porous structure.

Yttria-stabilized zirconia includes zirconia ($ZrO_2$) mixed with a minority amount of yttrium oxide ($Y_2O_3$). For example, one yttria-stabilized zirconia composition includes zirconia stabilized by about 7 wt. % to about 8 wt. % yttrium oxide, and may be referred to as 7-8 YSZ.

Rare earth oxides used in thermally insulative layer 29 include, for example, oxides of lutetium (Lu), ytterbium (Yb), thulium (Tm), erbium (Er), holmium (Ho), dysprosium (Dy), gadolinium (Gd), terbium (Tb), europium (Eu), samarium (Sm), promethium (Pm), neodymium (Nd), praseodymium (Pr), cerium (Ce), lanthanum (La), yttrium (Y), scandium (Sc), and combinations thereof. The same rare earth elements may also be useful when present as rare earth silicates, aluminates, or zirconates.

Article 24 also may include a contaminant layer 30 that has formed on TBC 28. Contaminant layer 30 may form on TBC 28 during use of article 24. For example, contaminant layer 30 may include siliceous minerals such as dust, sand, volcanic ashes, runway debris, or the like, which have been ingested during intake of air into a gas turbine engine. The siliceous materials may include, for examples, silica ($SiO_2$), alumina ($Al_2O_3$), calcia (CaO), magnesia (MgO), or the like. The siliceous minerals may melt or soften and cool to form contaminant layer 30 on TBC 28. In some examples, contaminant layer 30 may penetrate into the porous structure of thermally insulative layer 29. Contaminant layer 30 may also include materials generated in the turbine engine during normal operation, such as aluminum-containing materials from various seals or other material contained within the engines. Further, these materials may change chemical composition from their original form due to exposure to the high temperatures in the engine. Consequently, in some embodiments, oxides of aluminum or other metals within the engine may be contained within contaminant layer 30.

Although FIG. 1 illustrates the presence of contaminant layer 30 on TBC 28, in some embodiments, article 24 may not include a contaminant layer 30 on a portion of TBC 28. In such embodiments, LIBS system 10 may be utilized to determine an absence of contaminant layer 30, as described below with respect to FIG. 2.

Presence of contaminant layer 30 may interfere with determination of remaining life of TBC 28. As will be described with respect to FIGS. 4 and 5, remaining life of TBC 28 may be estimated by exposing TGO 34 to electromagnetic energy. Species within TGO 34, such as, for example, $Cr^{3+}$, may absorb the electromagnetic energy and fluoresce, and one or more characteristic of the fluorescence may be used to estimate the remaining life of TBC 28. For example, a dominant wavelength of fluorescence of the $Cr^{3+}$ in TGO 34 may be used to determine residual stress in TGO 34. The residual stress, then, may be used to estimate the remaining life of TBC 28.

However, contaminant layer 30 may interfere with exposing TGO 34 to electromagnetic energy. For example, components in contaminant layer 30 may absorb at least some of the electromagnetic energy and fluoresce, leading to measurement of the residual stress in contaminant layer 30 instead of TGO 34. In other examples, contaminant layer 30 may scatter the electromagnetic energy 38, absorb electromagnetic energy 38, or in some other way prevent sufficient energy from reaching TGO 34. Because of this, a determination that contaminant layer 30 is not present on a portion of TBC 28 or removal of a portion of contaminant layer 30, if present, may be necessary prior to exposing TGO 34 to electromagnetic energy to estimate remaining life of TBC 28.

LIBS system 10 is one example of a system that may be used to determine a presence of a component of TBC 28 or an absence of contaminant layer 30 and, if contaminant layer 30 is present, remove a portion of contaminant layer 30 from an outer surface 48 of TBC 28. Energy source 12 emits a beam of electromagnetic energy 38 of sufficient energy to ablate a portion 42 of article 24 when focused to a sufficient intensity. In some embodiments, as illustrated in FIG. 1B, portion 42 may include a portion of contaminant layer 30. In other embodiments, portion 42 may include a portion of TBC 28 (e.g., thermally insulative layer 29), alone or in combination with a portion of contaminant layer 30.

In some embodiments, beam 38 may include a relatively narrow range of wavelengths, such as a nominal wavelength plus or minus approximately 5 nanometers (nm), and energy source 12 may be said to emit substantially a first wavelength. For example, energy source 12 may include a Nd:YAG (Nd-doped yttrium aluminium garnet; $Nd:Y_3Al_5O_{12}$) laser that outputs electromagnetic energy with a nominal wavelength of approximately 355 nm, approximately 532 nm, or approximately 1064 nm. In other embodiments, energy source 12 may comprise a different type of laser, such as an Excimer laser, may output electromagnetic energy having a different nominal wavelength, or both.

In some embodiments, energy source 12 may emit beam 38 as a single pulse or a series of pulses. For example, each pulse may have a pulse length between approximately 10 nanoseconds (ns) and approximately 20 ns. In other embodiments energy source 12 may emit beam 38 as a pulse or series of pulses having a pulse length on the order of femtoseconds, picoseconds, or microseconds. In some embodiments, energy source 12 may be a continuous (non-pulsed) laser.

Energy source 12 may emit beam 38 with pulses of a sufficient energy to ablate a portion 42 (FIG. 1B) of contaminant layer 30 (and/or TBC 28) when focused to sufficient intensity. The effective pulse intensity may be a function of the pulse energy, pulse length, and focusing optics, such as objective lens 14. In some examples, the pulse energy may be greater than 100 mJ. In other examples, the pulse energy may be between approximately 5 mJ and approximately 75 mJ.

Energy source 12 emits beam 38 through objective lens 14, which focuses beam 38 into contaminant layer 30 (and/or TBC 28). In some embodiments, system 10 may include a mirror or other optical element in addition to or instead of objective lens 14 to focus beam 38. Objective lens 14 may focus beam 38 to a relatively small volume in order to increase a pulse intensity of the beam 38. In some embodiments, objective lens 14 may be translatable in one, two, or three dimensions to control a location at which beam 38 is focused.

In some embodiments, article 24 may be mounted or positioned on a movable stage 32, which may be used in conjunction with objective lens 14 to focus beam 38 at a desired position relative to article 24, e.g., at a position on or within contaminant layer 30 and/or TBC 28. Stage 32 may be translatable in one, two, or three dimensions.

In some embodiments, stage 32 and objective lens 14 may operate in conjunction to position article 24 relative to objective lens 14. For example, stage 32 may be translatable in two dimensions (e.g., an x-y plane in the coordinate system shown in FIG. 1A) and objective 14 may be translatable in one dimension (e.g., the z-axis in FIG. 1A). In other embodiments, each of objective lens 14 and stage 32 may be translatable in three dimensions and may work in conjunction to position the focal point of beam 38 relative to article 24. For example, stage 32 may provide relatively coarse positioning of article 32, while objective lens 14 provides relatively more precise positioning of the focal point of beam 38. As another example, stage 32 may provide relatively slow positioning of article 24 relative to beam 38, while objective lens 14 provides relatively faster positioning of beam 38 with respect to article 24. In some embodiments, one or both of objective lens 14 or stage 32 may move according to another coordinate system. For example, one or both of objective lens 14 or stage 32 may be positioned according to a polar coordinate system or a spherical coordinate system. In other words, positioning of one or both of objective lens 14 or stage 32 may include rotational positioning and not only linear positioning.

LIBS system 10 also includes a spectrometer 16, which may include a shutter 20 and a charge coupled device (CCD) 22. Spectrometer 16 may be used to detect and measure emitted electromagnetic energy 40, which is emitted by portion 42 ablated from contaminant layer 30 by beam 38, as will be described with respect to FIG. 2. Shutter 20 may open and close to prevent and allow emitted electromagnetic energy 40 to illuminate CCD 22. CCD 22 may be used to collect a spectrum of wavelengths of which emitted electromagnetic energy 40 is comprised. In some embodiments, spectrometer 16 may include a fixed grating chromator, which disperses emitted electromagnetic energy 40 in one or two dimensions along CCD 22 according to the frequency of photons in electromagnetic energy 40.

In some embodiments, spectrometer 16 may include a detector other than CCD 22 for detecting emitted electromagnetic energy 40. For example, spectrometer 16 may include a photomultiplier in combination with a filter or set of filters that separate wavelengths of the emitted electromagnetic energy 40 and pass a small set of wavelengths to the photomultiplier.

Although not shown in FIG. 1, in some embodiments, spectrometer 16 may be coupled to an optical fiber (not shown) that accepts electromagnetic energy 40 emitted by an ablated portion 42 of contaminant layer 30. The optical fiber may direct electromagnetic energy 40 to shutter 20 and spectrometer 16. In some embodiments, the optical fiber may act as a wavelength filter or a spatial filter which permits only a certain set of wavelengths or a energy 40 emitted from a certain spatial location to pass to shutter 20 and spectrometer 16.

In some embodiments, spectrometer 16 may collect a wide wavelength range of emitted electromagnetic energy 40, such as from approximately 1100 nm to 170 nm, to facilitate identification of the elements present in ablated portion 42 (FIG. 1B), which are emitting the electromagnetic energy 40. In other embodiments, spectrometer 16 may collect a subset of this range of electromagnetic energy that is known to contain characteristic wavelengths of a known element present in thermally insulative layer 29. For example, zirconium emits electromagnetic energy 40 at a wavelength of approximately 450 nm, among other wavelengths, and yttrium emits electromagnetic energy 40 at a wavelength of approximately 475 nm, among other wavelengths. In some embodiments, spectrometer 16 may collect a wavelength range approximately centered around one of these wavelengths or which includes at least one of these wavelengths.

LIBS system 10 further includes a control unit 18, which controls operation of energy source 12, objective 14, spectrometer 16 and stage 32. Additionally, control unit 18 may present a user interface that allows a user to interact with and control aspects of the operation of LIBS system 10. In some embodiments, control unit 18 may be a general computing device, such as a desktop computer, laptop computer, or the like executing on one or more microprocessors software stored in memory. In other embodiments, control unit 18 may be a special purpose computing device designed to interface only with LIBS system 10.

In some embodiments, control unit 18 may include software and hardware for interacting with a user, e.g., for receiving input from a user and outputting information to the user. For example, a user may change operational parameters of energy source 12, spectrometer 16, or positioning of objective 14 relative to stage 32. A user also may interact with a user interface provided by control unit 18 to manipulate and analyze data collected by spectrometer 16. During these processes, control unit 18 may present the user with user interface screens for interacting with LIBS system 10. The user may interact with the user interface presented by control unit 18 via input devices such as a keyboard, a touchscreen, a mouse, a microphone, or the like. Control unit 18 may output user interface screens for presentation to a user on, for example, an LCD screen, an LED array, a CRT screen, or a touchscreen display.

Control unit 18 may store control logic in memory that, in response to input received from a user via a user interface, directs the operation of LIBS system 10, including energy source 12, stage 32, and/or spectrometer 16. For example, control unit 18 may store software instructions in memory that, when executed, provide control logic for communicating commands to energy source 12 that specify an energy output (e.g., pulse energy, pulse power, pulse length, pulse number), to objective 14 and stage 32 that specify a relative position between objective 14 and stage 32, and to spectrometer 16 that specifies a timing for opening and closing shutter 20. In addition, control unit 18 may store software instructions in memory that provide commands to request and receive spectral data from spectrometer 16 during or upon completion of a LIBS process.

Control unit 18 may also store software instructions in memory that provide commands that are used to analyze the spectral data collected during the LIBS process. For example, control unit 18 may store software instructions that include exemplary LIBS spectra or characteristic emission wavelengths for a plurality of exemplary elements or TBC compositions, in order to provide reference spectra or emission wavelengths to which the collected LIBS spectra may be compared.

In some embodiments, control unit 18 may store software instructions in memory that provide commands for analyzing the spectral data collected during the LIBS process utilizing a cross-correlation technique. Cross-correlation may include comparing an electromagnetic energy spectrum collected from article 24 to a reference electromagnetic energy spectrum collected from a non-contaminated reference substrate including a chemical composition substantially similar to that of TBC 28 (e.g., substantially similar to thermally insulative layer 29). The reference spectrum may be stored in memory of control unit 18, and may have been collected during the same LIBS session that LIBS system 10 performs LIBS on article 24. In other embodiments, the reference spectrum may be stored in memory of control unit 18 and may have been collected previously, e.g., not during the same session that LIBS system 10 performs LIBS on article 24.

In some embodiments, collecting the reference spectrum during the same session the sample spectrum is collected, e.g., substantially immediately prior to performing LIBS on article 24, may be advantageous. For example, collecting the reference spectrum during the same session that LIBS is performed on article 24 may self-calibrate LIBS system 10. Self-calibration of LIBS system 10 may mitigate temporary or unexpected changes to system 10, such as misalignment of optical components of system 10, including objective lens 14; signal-to-noise ratio changes in spectrometer 16 or other components of system 10; spectral resolution changes in spectrometer 16; or the like. If not accounted for, such changes may result in degraded performance of LIBS system 10 compared to a system 10 that is self-calibrated, such as through a cross-correlation technique.

In performing cross-correlation, control unit 18 may compare the spectral content of at least a portion of the sample spectrum to the spectral content of at least a portion of the reference spectrum. For example, each of the sample spectrum and the reference spectrum may comprise a plurality of data points in an array, where each data point represents an intensity of the emitted electromagnetic energy 40 at a respective wavelength. Control unit 18 may determine a similarity between data points at the same wavelength for the reference spectrum and the sample spectrum and use this similarity to calculate a cross-correlation value.

In one embodiment, control unit 18 may first determine a mean intensity for the reference spectrum and a mean intensity for the sample spectrum. Control unit 18 then may determine a variance and sample standard deviation of the reference spectrum and a variance and sample standard deviation of the sample spectrum. Control unit 18 may subtract the mean intensity of the reference spectrum from each intensity value of the reference spectrum and subtract the mean intensity of the sample spectrum from each intensity value of the sample spectrum to determine a difference from the mean for each intensity value of the respective spectra. Control unit 18 then multiplies the differences from the mean for each intensity value of the reference spectrum and the sample spectrum point by point and sums the products. Finally, control unit 18 may multiply the standard deviations of the reference spectrum and the sample spectrum and normalize the summation of the products by this product of the standard deviations to determine the cross-correlation value. Control unit 18 may then store the cross-correlation value along with an index of the associated LIBS ablation cycle in memory, or may display the cross-correlation value on display for viewing by a user. For example, control unit 18 may display the cross-correlation value as a function of LIBS ablation cycle in a scatter diagram. Control unit 18 may utilize the cross-correlation value to determine when to stop ablation of article 24 by LIBS system 10. In other words, control unit 18 may utilize cross-correlation to determine when portion 42 includes a component of TBC 28 or when portion 42 does not include a component of contaminant layer 30, i.e., when article 24 is sufficiently clean that further ablation is not required. Further details regarding cross-correlation performed by control unit 18 will be described with reference to FIGS. 2 and 3.

Figure 2:
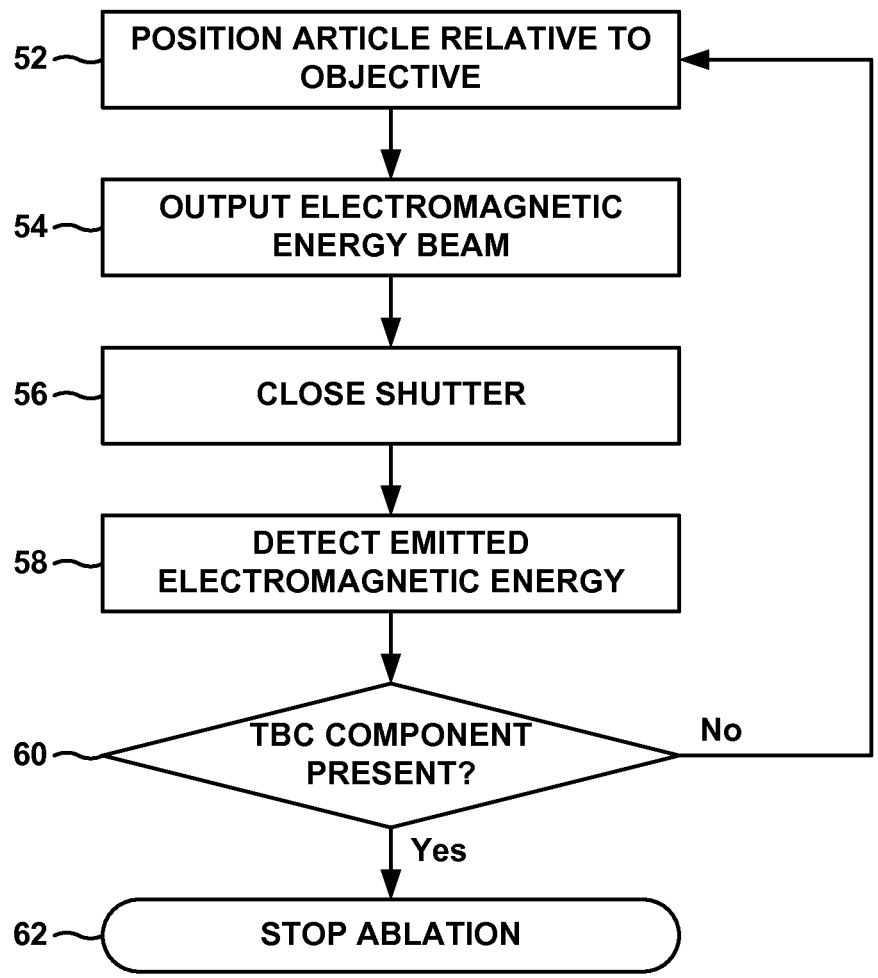
FIG. 2 is a flow diagram of an exemplary technique for determining whether a portion of an article includes a component of a thermal barrier coating (TBC) and, if a contaminant layer is present on the TBC, removing a portion of the contaminant layer from the TBC.

FIG. 2 illustrates an exemplary technique performed by LIBS system 10 for determining whether a portion of an article 24 includes a component of a TBC 28 or whether a contaminant layer 30 is present on TBC 28 and, if contaminant layer 30 is present, removing a portion of contaminant layer 30 from article 24. Initially, once an article 24 is coupled to stage 32, article 24 is positioned relative to objective lens 14 (and, ultimately, the path of beam 38) by moving at least one of stage 32 or objective lens 14 (52). In some embodiments, control unit 18 may control the positioning, e.g., a user may input a command via a user interface that indicates an article 24 is coupled to stage 32 and control unit 18 may automatically position article 24 relative to objective lens 14 (52). In other embodiments, a user may manually position stage 32 (or article 24 on stage 32) relative to objective lens 14, e.g., by actuating one or more knob, levers, or the like to cause stage 32 to move relative to objective lens 14 (52). In other embodiments, a combination of manual positioning of stage 32 and/or objective lens 14 by a user and automatic positioning of stage 32 and/or objective lens 14 by control unit 18 may combine to position article 24 relative to objective lens 14 (52).

Once article 24 is positioned relative to objective lens 14 such that beam 38 of electromagnetic energy 38 is focused proximate to a surface of contaminant layer 30 or TBC 28, control unit 18 causes energy source 12 to output a beam 38 in a single pulse or a set of pulses (54). In some embodiments, control unit 18 may automatically (e.g., without intervention of a user) cause energy source 12 to output beam 38 once article 24 is positioned relative to objective lens 14 such that beam 38 is focused proximate to a surface of contaminant layer 30 and/or TBC 28. In other embodiments, a user may enter a command via a user interface that causes control unit 18 to cause energy source 12 to output beam 38.

Beam 38 comprises a sufficient pulse intensity to ablate portion 42, which may include a portion of contaminant layer 30 and/or a portion of TBC 28. The size, e.g., volume, of portion 42 that is ablated by each pulse may be a function of a variety of variables, such as, for example, pulse energy, pulse power, pulse size, pulse length (duration), objective lens 14, composition of contaminant layer 30 and/or TBC 28, or the like. A user may enter the desired pulse parameters prior to entering the command that causes control unit 18 to cause energy source 12 to output beam 38. For example, the user may select desired pulse parameters from a list of feasible pulse parameters, may enter pulse parameters into a text box, or the like. In other embodiments, a memory in control unit 18 may store predetermined pulse parameters and may automatically load the pulse parameters from memory and cause energy source 12 to emit beam 38 having such parameters.

Ablation of portion 42 may occur when beam 38 heats portion 42 of contaminant layer 30 and/or TBC 28 to a sufficient temperature to vaporize portion 42 and eject portion 42 from contaminant layer 30. Portion 42 may form a plasma above the surface of article 24. The high temperature (e.g., between approximately 5,000 K and approximately 100,000 K) of the resulting plasma may dissociate and ionize the material in portion 42, resulting in free electrons that may absorb the remaining laser pulse through an inverse Bremsstrahlung process. The plasma emits electromagnetic energy in a substantially continuous spectrum for a time after beam 38 ceases. This substantially continuous spectrum may not be useful for determining the composition of portion 42, and shutter 20 of spectrometer 16 may be closed during this time to prevent the emitted electromagnetic energy 40 comprising the substantially continuous spectrum from reaching CCD 22 (56). As the plasma cools, the free electrons in the plasma may rebind to the atomic elemental components of portion 42. During this process, the free electrons and atoms emit electromagnetic energy 40 comprising strong peaks at certain wavelengths corresponding to elements in portion 42. At this time, shutter 20 may be open to allow emitted electromagnetic energy 40 including the strong peaks to reach CCD 22. CCD 22 detects the emitted electromagnetic energy 40 (58), and may convert the emitted electromagnetic energy 40 to a signal, such as, for example, a voltage or current signal representative of a spectrum of emitted electromagnetic energy 40, which is transmitted to control unit 18. In some embodiments, emission of strong atomic peaks may be sufficient to overcome the continuous background such that shutter 20 can remain open, as it is not necessary to prevent the initial, substantially continuous spectrum from reaching CCD 22.

Control unit 18 receives the signal from spectrometer 16 and analyzes the signal to determine whether a component of TBC 28 (e.g., thermally insulative layer 29) is present in the ablated portion 42 (60). In some embodiments, control unit 18 may identify substantially all components of portion 42 based on the emitted electromagnetic energy 40. For example, control unit 18 may store a database of characteristic emission wavelengths for a plurality of elements, including elements in contaminant layer 30.

In other embodiments, control unit 18 may simply analyze the signal received from spectrometer 16 and identify the presence or absence in portion 42 of at least one component of thermally insulative layer 29. For example, thermally insulative layer 29 may comprise yttria-stabilized zirconia, which includes yttrium and zirconium. Control unit 18 may store at least one characteristic emission wavelength for one or both of yttrium and zirconium in memory, and may analyze the signal from spectrometer 16 to determine whether one or more of these characteristic emission wavelengths are present in the signal.

In some embodiments, control unit 18 may utilize cross-correlation to analyze the signal received from spectrometer 16 and determine whether article 24 is sufficiently clean (e.g., whether portion 42 is sufficiently free of a component of contaminant layer 30 or whether portion 42 includes components of thermally insulative layer 29) such that LIBS system 10 may stop ablating portions 42 of article 24. In a cross-correlation technique, control unit 18 compares a reference spectrum collected from a non-contaminated reference substrate including a chemical composition substantially similar to that of thermally insulative layer 29 to the signal detected from ablated portion 42 (a "sample spectrum").

Control unit 18 may collect the reference spectrum prior to performing on article 24 the technique illustrated in FIG. 2. In some embodiments, control unit 18 collects the reference spectrum substantially immediately prior to performing the technique illustrated in FIG. 2. For example, LIBS system 10 may be used to collect a reference spectrum from the reference substrate during the same operational session in which LIBS system 10 ablates a portion 42 of article 24 to determine whether a contaminant layer 30 is present on article 24. In other embodiments, control unit 18 may store in memory a reference spectrum that has been collected previously, e.g., in a previous session.

The reference spectrum may be collected from a non-contaminated reference substrate, which includes a chemical composition substantially similar to that of thermally insulative layer 29 and does not include contaminant layer 30, and which is attached to stage 32 and positioned such that beam 38 may be used to ablate a portion of the reference sample. Similar to ablated portion 42 of article 24, the ablated portion of the reference sample may form a plasma. As the plasma cools, the free electrons in the plasma rebind to the atomic elemental components of the ablated portion of the reference sample. During this process, the free electrons and atoms emit electromagnetic energy comprising strong peaks at certain wavelengths corresponding to elements in the ablated portion of the reference sample.

Spectrometer 16 may sense at least a portion of the electromagnetic energy emitted by the ablated portion of the reference sample and convert the emitted electromagnetic energy 40 to a signal, such as, for example, a voltage or current signal representative of a spectrum of emitted electromagnetic energy 40, which is transmitted to control unit 18. Control unit 18 may digitize the voltage or current signal and store the digitized values in an array comprising a plurality of wavelength values of the emitted electromagnetic energy and an associated intensity value for each wavelength.

Control unit 18 then utilizes at least a portion of the digitized values representative of the reference spectrum (the "reference spectrum") to determine a cross-correlation value for a sample spectrum collected from article 24. Upon receiving a signal representative of emitted electromagnetic energy 40, control unit 18 may cross-correlate the sample spectrum with the reference spectrum to determine a cross-correlation value. In cross-correlating the sample spectrum with the reference spectrum, control unit 18 may compare the spectral content of the sample spectrum to the spectral content of the reference spectrum. For example, control unit 18 may determine a similarity between data points at the same wavelength for the reference spectrum and the sample spectrum and use this similarity to calculate a cross-correlation value.

In one embodiment, control unit 18 may first determine a mean intensity for the reference spectrum and a mean intensity for the sample spectrum. Control unit 18 then may determine a variance and sample standard deviation of the reference spectrum and a variance and sample standard deviation of the sample spectrum. Control unit 18 may subtract the mean intensity of the reference spectrum from each intensity value of the reference spectrum and subtract the mean intensity of the sample spectrum from each intensity value of the sample spectrum to determine a difference from the mean for each intensity value of the respective spectra.

Control unit 18 then multiplies the differences from the mean for each intensity value of the reference spectrum and the sample spectrum point by point and sums the products of this point-by-point multiplication. Finally, control unit 18 may multiply the standard deviations of the reference spectrum and the sample spectrum and normalize the summation of the products by this product of the standard deviations to determine the cross-correlation value. Control unit 18 may then store the cross-correlation value along with an index of the associated LIBS ablation cycle in memory, or may display the cross-correlation value on display for viewing by a user. For example, control unit 18 may display the cross-correlation value as a function of LIBS ablation cycle in a scatter diagram. Control unit 18 may utilize the cross-correlation value to determine when to stop ablation of article 24 by LIBS system 10. Further details regarding cross-correlation performed by control unit 18 will be described with reference to FIG. 3.

In some embodiments, control unit 18 may automatically determine whether a component of thermally insulative layer 29 is present in portion 42. For example, control unit 18 may automatically apply an algorithm, such as cross-correlation, to the signal received from spectrometer 18 to determine is a component of thermally insulative layer 29 is present in portion 42. In other embodiments, control unit 18 may display the spectrum detected by spectrometer 18 to a user in graphical, tabular or numerical form and the user may make a determination of whether portion 42 contains any elements present in thermally insulative layer 29.

In some embodiments, when control unit 18 or a user determines an element from thermally insulative layer 29 is not present in portion 42, this may indicate that a contaminant layer 30 is present on TBC 28. The technique then may return to step (52) and article 24 may be repositioned relative to objective lens 14 to reposition the focal point of beam 38 to a new location proximate to a surface of contaminant layer 30. Repositioning of article 24 relative to objective lens 14 may be necessary because portion 42 was ablated from the surface of contaminant layer 30, thus changing the position of the surface of contaminant layer 30. Accordingly, article 24 may be repositioned to be closer to objective lens 14 by an amount approximately equal to the depth of a depression 44 left by ablated portion 42. In some embodiments, this may be approximately 1 micron. As described above with respect to step (52), positioning of article 24 relative to objective lens 14 may be accomplished automatically (e.g., without user intervention) under control of control unit 18, may be accomplished manually by a user, or may be accomplished cooperatively by control unit 18 and a user. In some embodiments, the repositioning of article 24 relative to objective lens 14 may be accomplished automatically under control of control unit 18, while the initial positioning of article relative to objective lens 14 may have been accomplished by a user or by a user in conjunction with control unit 18.

In other embodiments, article 24 may not need to be repositioned relative to objective lens 14, and the technique may return directly to step (54). Regardless of whether the technique returns first to step (52) or proceeds directly to step (54), control unit 18 may automatically or under control of the user cause energy source 12 to output a beam of electromagnetic energy 38 (54). Beam 38 may again comprise a pulse or series of pulses of sufficient intensity to ablate a second portion of contaminant layer 30 (not shown in FIG. 1B). The pulse characteristics, such as pulse energy, pulse power, pulse length (duration) and pulse area may be the same or different than those used during the first iteration of step (54). The second ablated portion may be located substantially below depression 44 formed by ablation of portion 42, and may be closer to thermally insulative layer 29 than portion 42 was. In effect, the sequential ablation of portions of contaminant layer 30 forms a hollow extending from outer surface 46 of contaminant layer 30, into layer 30, and towards thermally insulative layer 29.

Upon ablation of the second portion of contaminant layer 30, the second portion may form a plasma above the surface of contaminant layer 30. The high temperature (e.g., between approximately 5,000 K and approximately 100,000 K) of the resulting plasma may dissociate and ionize the material of the second portion, resulting in free electrons that may absorb the remaining laser pulse through an inverse Bremsstrahlung process. The plasma emits electromagnetic energy in a substantially continuous spectrum for a time after beam 38 ceases. This substantially continuous spectrum may not be useful for determining the composition of the second portion, and shutter 20 of spectrometer 16 may be closed during this time to prevent the emitted electromagnetic energy 40 comprising the substantially continuous spectrum from reaching CCD 22 (56). As the plasma cools, the free electrons in the plasma may rebind to the atomic elemental components of the second portion. During this process, the free electrons and atoms emit electromagnetic energy 40 comprising strong peaks at certain wavelengths corresponding to elements in the second portion. At this time, shutter 20 may be open to allow emitted electromagnetic energy 40 including the strong peaks to reach CCD 22. CCD 22 detects the emitted electromagnetic energy 40 (58), and may convert the emitted electromagnetic energy 40 to a signal, such as, for example, a voltage or current signal, which is transmitted to control unit 18.

Control unit 18 receives the signal from spectrometer 16 and analyzes the signal to determine whether a component of TBC 28 (e.g., thermally insulative layer 29) is present in the ablated second portion (60). In some embodiments, control unit 18 may identify substantially all components of the second portion based on the emitted electromagnetic energy 40, while in other embodiments, control unit 18 may simply analyze the signal received from spectrometer 16 and identify the presence or absence in the second portion of at least one component of thermally insulative layer 29. For example, thermally insulative layer 29 may comprise yttria-stabilized zirconia, which includes yttrium and zirconium. Control unit 18 may store at least one characteristic emission wavelength for one or both of yttrium and zirconium in memory, and may analyze the signal from spectrometer 16 to determine whether one or more of these characteristic emission wavelengths are present in the signal.

In some embodiments, control unit 18 may automatically determine if a component of thermally insulative layer 29 is present in the second portion. For example, control unit 18 may automatically apply an algorithm, such as cross-correlation, to the signal received from spectrometer 18 to determine whether a component of thermally insulative layer 29 is present in the second portion (60). In other embodiments, control unit 18 may display the spectrum detected by spectrometer 18 to a user in graphical, tabular or numerical form and the user may make a determination of whether the second portion contains any elements present in thermally insulative layer 29.

When control unit 18 or a user determines that the second portion does not contain an element of thermally insulative layer 29, the technique may again return to one of step (52) or step (54), and the process may repeat to remove a third ablated portion.

However, when control unit 18 or a user determines that an element of thermally insulative layer 29 is present in the ablated portion 42 (or subsequent ablated portions), the technique may end (62). The presence in an ablated portion 42 of an element from thermally insulative layer 29 may indicate that a contaminant layer 30 is not present on a portion of TBC 28 or may indicate that a portion of contaminant layer 30 extending substantially from outer surface 46 of contaminant layer 30 to outer surface 48 of thermally insulative layer 29 has been ablated to form a hollow extending from outer surface 46 to outer surface 48. This may provide a window in contaminant layer 30 through which subsequent spectroscopic investigations on TBC 28 may be performed.

In some embodiments, as will be described in further detail with reference to FIG. 6, the technique may include causing energy source 12 to output a beam of electromagnetic energy 38 at least one additional time to ensure that contaminant layer 30 has been fully removed to form the hollow extending to thermally insulative layer 29. The technique may then end (62).

Figure 3:
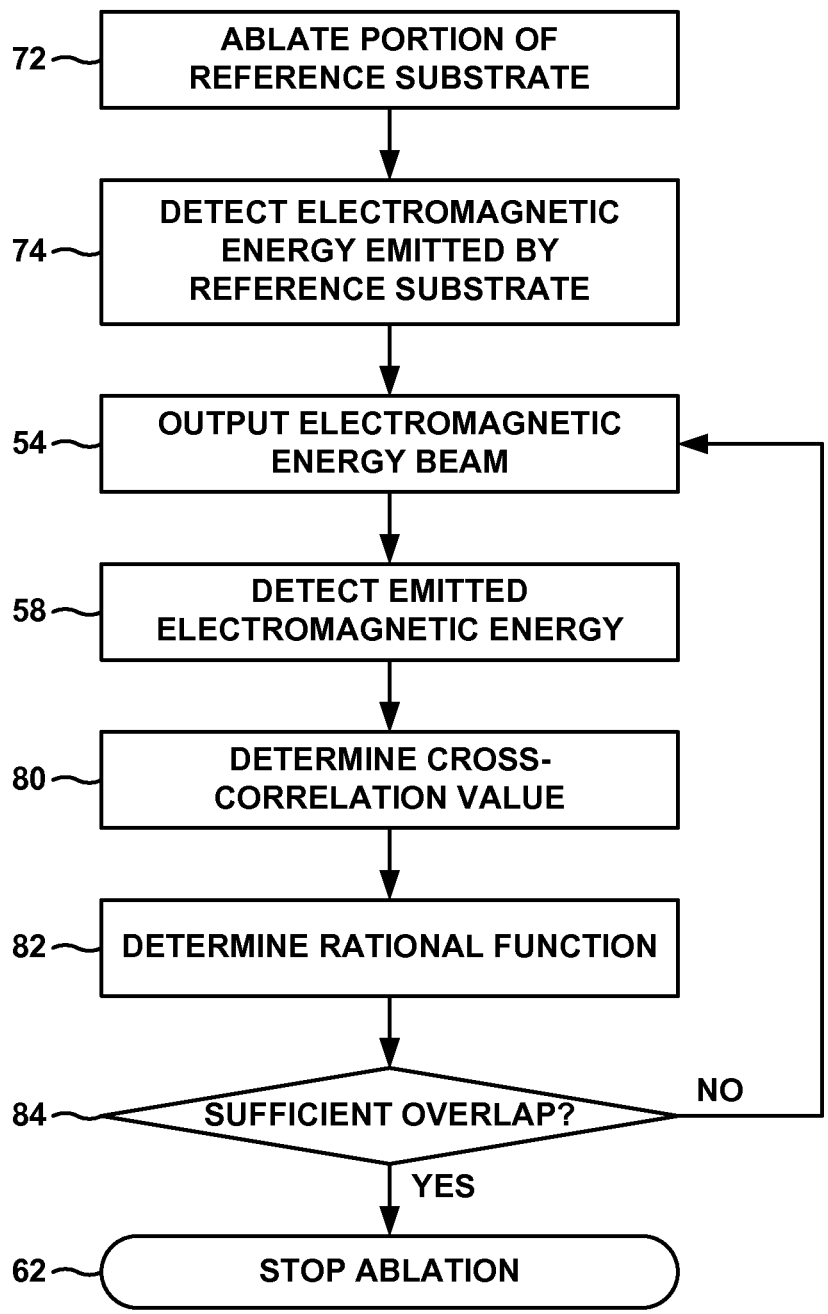
FIG. 3 is a flow diagram of an exemplary technique for determining whether a component of a thermal barrier coating (TBC) or a component of a contaminant layer is present in an ablated portion of an article including a TBC.

FIG. 3 illustrates one embodiment of a cross-correlation technique that LIBS system 10, and more particularly, control unit 18, may utilize to determine whether a component of TBC 28, or contaminant layer 30, is present in portion 42 (60), and when to stop ablation of article 24 (62). Initially, a reference substrate is positioned relative to objective lens 14

(and, ultimately, the path of beam 38 (FIGS. 1A and 1B)) by moving at least one of stage 32 or objective lens 14. In some embodiments, control unit 18 may control the positioning of the reference substrate, e.g., a user may input a command via a user interface that indicates the reference substrate is coupled to stage 32 and control unit 18 may automatically position the reference substrate relative to objective lens 14. In other embodiments, a user may manually position stage 32 (or the reference substrate on stage 32) relative to objective lens 14, e.g.; by actuating one or more knob, levers, or the like to cause stage 32 to move relative to objective lens 14. In other embodiments, a combination of manual positioning of stage 32 and/or objective lens 14 by a user and automatic positioning of stage 32 and/or objective lens 14 by control unit 18 may combine to position the reference substrate relative to objective lens 14.

The reference substrate may include a chemical composition substantially similar to a chemical composition of thermally insulative layer 29. The reference substrate does not include a contaminant or a contaminant layer on a surface of the substrate. In some embodiments, the reference substrate may include at least one of yttria-stabilized zirconia, yttria-stabilized hafnia, rare earth oxides, aluminates, silicates, zirconates, a rare earth oxide-stabilized zirconia, a rare earth oxide-stabilized hafnia.

Once the reference substrate is in position relative to the path of beam 38 such that beam 38 is focused proximate to a surface of the reference substrate, control unit 18 may cause energy source 12 to output beam 38 of sufficient intensity to ablate a portion of the reference substrate. In some embodiments, control unit 18 may automatically (e.g., without intervention of a user) cause energy source 12 to output beam 38, while in other embodiments, a user may enter a command via a user interface that causes control unit 18 to cause energy source 12 to output beam 38.

Similar to ablation of portion 42, described above with reference to FIG. 2, ablation of a portion of the reference substrate may occur when beam 38 heats a portion of the reference substrate to a sufficient temperature to vaporize the portion and eject the portion from the reference substrate. The portion of the reference substrate may form a plasma above the surface of the reference substrate. The high temperature (e.g., between approximately 5,000 K and approximately 100,000 K) of the resulting plasma may dissociate and ionize the material in the portion, resulting in free electrons that may absorb the remaining laser pulse through an inverse Bremsstrahlung process. The plasma emits electromagnetic energy in a substantially continuous spectrum for a time after beam 38 ceases. This substantially continuous spectrum may not be useful for determining the composition of the portion of the reference substrate, and shutter 20 of spectrometer 16 may be closed during this time to prevent the emitted electromagnetic energy comprising the substantially continuous spectrum from reaching CCD 22. As the plasma cools, the free electrons in the plasma may rebind to the atomic elemental components of the ablated portion of the reference substrate. During this process, the free electrons and atoms emit electromagnetic energy comprising strong peaks at certain wavelengths corresponding to elements in the ablated portion. At this time, shutter 20 may be open to allow the emitted electromagnetic energy including the strong peaks to reach CCD 22. CCD 22 detects the emitted electromagnetic energy, and may convert the emitted electromagnetic energy to a signal, such as, for example, a voltage or current signal representative of a spectrum of the emitted electromagnetic energy, which is transmitted to control unit 18 (74). In some embodiments, emission of strong atomic peaks may be sufficient to overcome the continuous background such that shutter 20 can remain open, as it is not necessary to prevent the initial, substantially continuous spectrum from reaching CCD 22.

Control unit 18 may store in memory as a plurality of values in a data array the signal representative of the spectrum of the electromagnetic energy emitted by the ablated portion of the reference substrate. For example, the plurality of values in the data array may include wavelengths of the emitted electromagnetic energy and associated intensity values for the respective wavelengths.

Although FIG. 3 illustrates ablating a portion of the reference substrate (72) and detecting electromagnetic energy emitted by the reference substrate (74) as the initial steps in the cross-correlation technique, in other embodiments, the technique may not include these initial steps, or these steps may be performed at a time previous to and separated from the performance of the remainder of the steps illustrated in FIG. 3. For example, a reference spectrum may be collected on another LIBS system or the same LIBS system 10 at a time prior to performing the remaining steps of FIG. 3. The reference spectrum collected in this manner may be stored in a memory of control unit 18 and reused for multiple operating sessions during which LIBS system 10 performs ablation of a portion 42 of article 24. While this may simplify subsequent use of LIBS system 10 to ablate a portion 42 of article 24 (because a reference spectrum may not be collected before ablation of a portion 42 of each new article 24), such a process may not self-calibrate LIBS system 10.

Once the reference spectrum has been collected or stored in a memory of control unit 18, article 24 may be coupled to stage 32 and positioned relative to objective 14 such that beam 38 is focused proximate to a surface of contaminant layer 30 of thermally insulative layer 29. Control unit 18 then may automatically (e.g., without intervention of a user) or under control of a user cause energy source 32 to output a beam 38 having sufficient energy to ablate a portion 42 or article 24 (54).

As described above, portion 42 may include a portion of contaminant layer 30 and/or a portion of thermally insulative layer 29. Ablation of portion 42 may occur when beam 38 heats portion 42 to a sufficient temperature to vaporize portion 42 and eject portion 42 from contaminant layer 30 and/or TBC 28. Portion 42 may form a plasma above the surface of article 24 and emit electromagnetic energy in a substantially continuous spectrum for a time after beam 38 ceases. This substantially continuous spectrum may not be useful for determining the composition of portion 42, and shutter 20 of spectrometer 16 may be closed during this time to prevent the emitted electromagnetic energy 40 comprising the substantially continuous spectrum from reaching CCD 22. As the plasma cools, the free electrons in the plasma may rebind to the atomic elemental components of portion 42. During this process, the free electrons emit electromagnetic energy 40 comprising strong peaks at certain wavelengths corresponding to elements in portion 42 and the atoms emit electromagnetic energy 40 comprising strong atomic transitions within the atom. At this time, shutter 20 of spectrometer 16 may be open to allow emitted electromagnetic energy 40 including the strong peaks to reach CCD 22. CCD 22 detects the emitted electromagnetic energy 40 (58), and may convert the emitted electromagnetic energy 40 to a signal, such as, for example, a voltage or current signal, which is transmitted to control unit 18.

Spectrometer 16 or control unit 18 may digitize the signal to produce an array of wavelength values and associated intensity values representative of the spectrum of emitted electromagnetic energy 40 (the "sample spectrum"). Control unit 18 may utilize at least a portion of the sample spectrum and at least a portion of the reference spectrum to determine a cross-correlation value between the sample spectrum and the reference spectrum (80).

Control unit 18 may determine the cross-correlation value by comparing an overlap or similarity between respective intensity values of the sample spectrum and the reference spectrum (at substantially the same wavelengths). Generally, the cross-correlation value is representative of an amount of similarity or dissimilarity between the reference spectrum and the sample spectrum.

In some embodiments, control unit 18 may utilize substantially all the reference spectrum and substantially all the sample spectrum in the cross-correlation technique. For example, the reference spectrum and the sample spectrum may comprise substantially similar wavelength values (e.g., 170 nm to 1100 nm), and control unit 18 may utilize substantially all the wavelength values in the cross-correlation technique. In other embodiments, control unit 18 may select a portion of the reference spectrum and a portion of the sample spectrum and compare these portions to each other in the cross-correlation technique. For example, control unit 18 may select a plurality of wavelength values and corresponding intensity values for the reference spectrum and the same plurality of wavelength values for the sample spectrum. The plurality of wavelength values may be substantially the same for the reference spectrum and the sample spectrum. In this way, control unit 18 may cross-correlate portions of the reference spectrum and the sample spectrum that comprise substantially identical wavelength values.

In some embodiments, the plurality of wavelength values in the selected portions may be centered around one or more wavelength of interest. For example, as described above, zirconium may emit electromagnetic energy having a wavelength of approximately 450 nm and yttrium may emit electromagnetic energy having a wavelength of approximately 475 mm. Thus, in some embodiments, control unit 18 may select a portion of the reference spectrum and a portion of the sample spectrum including wavelength values centered around 450 nm, centered around 475 nm, or including both 450 nm and 475 nm. Control unit 18 may then cross correlate the selected portion of the reference spectrum and the selected portion of the sample spectrum.

In some embodiments, control unit 18 may determine a cross-correlation value by first determining a mean intensity value for the portion of the reference spectrum according to Equation 1.

$$\overline{R} = \frac{\sum_{i=1}^{N} R_i}{N} \qquad \text{Equation 1}$$

where $\overline{R}$ is the mean intensity value, $R_i$ represents the intensity values for each of the plurality of wavelengths in the reference spectrum and N is the number of wavelength values in the portion of the reference spectrum. Control unit 18 also determines a mean intensity value for portion of the sample spectrum according to Equation 2.

$$\overline{T} = \frac{\sum_{i=1}^{N} T_i}{N} \qquad \text{Equation 2}$$

where $\overline{T}$ is the mean intensity value, $T_i$ represents the intensity values for each of the plurality of wavelengths in the sample spectrum and N is the number of wavelength values in the portion of the sample spectrum (and is equal to the number of wavelength values in the reference spectrum).

Control unit 18 then determines the variance of the portion of the reference spectrum, $\overline{R'^2}$, according to Equation 3 and the sample standard deviation of the portion of the reference spectrum, $s_R$, according to Equation 4.

$$\overline{R'^2} = \frac{\sum_{i=1}^{N}(R_i - \overline{R})^2}{N-1} \qquad \text{Equation 3}$$

$$s_R = \sqrt{\overline{R'^2}} \qquad \text{Equation 4}$$

Control unit 18 then determines the variance of the portion of the sample spectrum, $\overline{T'^2}$, according to Equation 5 and the sample standard deviation of the portion of the sample spectrum, $s_T$, according to Equation 6.

$$\overline{T'^2} = \frac{\sum_{i=1}^{N}(T_i - \overline{T})^2}{N-1} \qquad \text{Equation 5}$$

$$s_T = \sqrt{\overline{T'^2}} \qquad \text{Equation 6}$$

Control unit 18 then utilizes the mean values, $\overline{T}$ and $\overline{R}$, the individual intensity values, $T_i$ and $R_i$, and the sample standard deviations, $s_R$ and $s_T$, to determine a cross correlation value, c, for the portion of the sample spectrum and the portion of the reference spectrum according to Equation 7.

$$c = \frac{\sum_{i=1}^{N}(T_i - \overline{T})(R_i - \overline{R})}{s_R s_T} \qquad \text{Equation 7}$$

In this embodiment, the cross correlation value is calculated by point-by-point multiplication of the intensity values of the portions of the reference and sample spectrums. In other words, control unit 18 selects a wavelength value, determines a difference from the mean for the reference spectrum intensity and sample spectrum intensity at this wavelength value, and multiplies the difference from the mean of the reference spectrum intensity with the difference from the mean of the sample spectrum intensity. Control unit 18 repeats this process for each of the N wavelengths in the portions of the reference and sample spectra, and sums the products of the point-by-point multiplication. Control unit 18 then normalizes the sum of the products of the point-by-point multiplication by the product of the sample standard deviations of the portions of the reference and sample spectra, and the result is the cross-correlation value, c.

Such a technique for determining a cross correlation value is one example of determining a cross correlation value. In other embodiments, the cross correlation value may be determined via another technique and/or other equations. In general, control unit 18 may utilize any cross-correlation technique which compares the similarity or dissimilarity of a portion of the reference spectrum and the sample spectrum.

Control unit 18 may store in memory a data array comprising the cross correlation value and the associated ablation cycle (e.g., whether the sample spectrum was collected from a first ablation of a portion 42 of article 24, a second ablation of a portion 42 of article, or the like).

Once control unit 18 has determined a cross correlation value for each of at least two sample spectra (to provide at least two points in the data array), control unit 18 may utilize the cross correlation values for the at least two sample spectra to fit an exponential function to a data array of the ablation cycles and associated cross correlation values. (82). The data array may be visualized as a scatter plot of the cross correlation values versus the ablation cycle, and control unit 18 may display such a plot for a user via a user interface device, such as a monitor or other display device. It is believed that the cross correlation value substantially monotonically increases and asymptotically approaches a value between approximately 0.5 and approximately 1 as the similarity between the sample spectrum and the reference spectrum increases (e.g., as article 24 is cleaned). Based on this assumption, control unit 18 may determine the fit of an exponential function to the data array and utilize the exponential function to estimate whether a portion 42 represented by the most recently collected sample spectrum includes a component of thermally insulative layer 29 and/or includes a component of contaminant layer 29. In other words, control unit 18 may utilize the exponential function to determine whether to stop ablation of article 24.

The exponential function may comprise three fit parameters, A, B, and T, as shown in Equation 8.

$$N(x) = A(1 - e^{-x/T}) + B \qquad \text{Equation 8}$$

where x is the ablation cycle, B is the initial condition when x=0, A+B is the asymptotic value as x goes to infinity, and T is the time scale for the change in the cross-correlation value and is the value of x (the ablation cycle) at which change has occurred in the cross correlation value equal to approximately 63% of the asumptotic cross correlation value.

Control unit 18 may fit the exponential function to the data array by determining A, B, and T via a regression analysis, such as linear regression, nonlinear regression, least squares regression, or the like.

Once control unit 18 has determined an exponential function that fits the data array, control unit 18 may utilize the exponential function and/or the most recently determined cross correlation value to determine whether there is sufficient overlap between the reference spectrum and sample spectrum to stop ablation of article 24 (84). Sufficient overlap between the reference spectrum and sample spectrum, as evidenced by the cross correlation value, may indicate a composition of portion 42 is sufficiently similar to the reference substrate. Stated another way, sufficient overlap between the reference spectrum and sample spectrum may indicate that portion 42 includes at least one component of thermally insulative layer 29 and/or does not include substantial amounts of component(s) of contaminant layer 30.

In some embodiments, control unit 18 may utilize the exponential function to predict an approximate value that the cross correlation value will asymptotically approach as the number of ablation cycles of article 24 increases towards infinity (e.g., by determining the limit of the exponential function as the ablation cycles go to infinity, which is equal to A+B). Control unit 18 may multiply this approximate asymptotic value by a predetermined fraction or percentage to calculate a threshold cross correlation value above which control unit 18 will determine overlap between the reference spectrum and the sample spectrum is sufficient to stop ablation of article 24. In some embodiments, this fraction or percentage may be between approximately 0.6 (60%) and approximately 0.7 (70%). Control unit 18 may then compare the most recently calculated cross correlation value to the threshold cross correlation value to determine whether there is sufficient overlap between the reference spectrum and sample spectrum to stop ablation of article 24 (84).

In some embodiments, control unit 18 may utilize T as the threshold cross correlation value. As stated above, T is equal to approximately 63% of the asymptotic cross correlation value. Control unit 18 may compare the most recently calculated cross correlation value to T (the threshold cross correlation value) to determine whether there is sufficient overlap between the reference spectrum and sample spectrum to stop ablation of article 24 (84).

In some embodiments, control unit 18 may determine a change between the current exponential function fit to the data array and a prior exponential function fit to a data array that did not include the most recent cross correlation value. In this way, control unit 18 may determine how inclusion of the most recent cross correlation value changed the exponential function that is fit to the cross correlation data array. It is expected that as additional cross correlation values are determined (for additional ablation cycles) the fit of a exponential function to the cross correlation data array may improve, and addition of subsequent cross correlation values will result in smaller change between the current exponential function and an exponential function fit to the previous cross correlation data array. Accordingly, control unit 18 may calculate a percent change or fractional change in one or more characteristic of the exponential function (e.g., a fractional change or percent change of one or more of A, B, or T) and compare the calculated percent change or fractional change to a threshold percent change or fractional change. Based on the result of the comparison, control unit 18 may determine whether the exponential function is sufficiently stable (e.g., the calculated percent change or fractional change is less than or equal to the threshold percent change or fractional change). Control unit 18 may utilize a determination of the stability of the exponential function alternatively or in addition to the determination of a threshold cross correlation value to determine whether there is sufficient overlap between the reference spectrum and sample spectrum to stop ablation of article 24 (84).

In some embodiments, control unit 18 may alternatively or additionally determine an approximate rate of change of the cross correlation value based on the exponential function. For example, control unit 18 may determine a derivative of the exponential function at the most recent ablation cycle. Control unit 18 then may compare the derivative of the exponential function at the most recent ablation cycle to a threshold rate of change (or threshold derivative) of the cross correlation value. When the derivative of the exponential function is less than or substantially equal to the threshold derivative, control unit 18 may determine that the cross correlation value indicates there is sufficient overlap between the reference spectrum and sample spectrum to stop ablation of article 24 (84). On the other hand, when the derivative of the exponential function is greater than the threshold derivative, control unit 18 may determine that the cross correlation value indicates there is not sufficient overlap between the reference spectrum and sample spectrum to stop ablation of article 24.

In some examples, control unit 18 may utilize an approximate rate of change of the cross correlation value in addition to at least one the cross correlation value or the change in the exponential function to determine whether there is sufficient overlap between the reference spectrum and sample spectrum to stop ablation of article 24. For example, control unit 18 may first determine whether the cross correlation value is above a threshold cross correlation value and then determine whether the approximate rate of change of the cross correlation value is below a threshold rate of change. When the answer to both of these inquiries is yes, control unit 18 may determine that there is sufficient overlap between the reference spectrum and the sample spectrum, and may stop ablation of article 24 (62). When the answer to at least one of these inquiries is no, control unit 18 may determine that there is not sufficient overlap between the reference spectrum and the sample spectrum, and may return to step (54) to ablate another portion 42 of article 24.

When control unit 18 determines that there is not sufficient overlap between the reference spectrum and the sample spectrum, control unit 18 may cause energy source 32 to output an additional beam of electromagnetic energy 38 to ablate another portion 42 of article 24 (54). CCD 22 detects the emitted electromagnetic energy 40 (58), and may convert the emitted electromagnetic energy 40 to a signal, such as, for example, a voltage or current signal, which is transmitted to control unit 18. Spectrometer 16 or control unit 18 may digitize the signal to produce an array of wavelength values and associated intensity values representative of the spectrum of emitted electromagnetic energy 40 (the "sample spectrum"). Control unit 18 may utilize the sample spectrum and the reference spectrum to determine a cross-correlation value between the sample spectrum and the reference spectrum (80). Control unit 18 may store this cross-correlation value and the associated ablation cycle in the data array of cross-correlation values and ablation cycles.

Control unit 18 may utilize the cross-correlation values stored in the data array to fit a exponential function to the data array (82). As described above, control unit 18 may determine the fit of an exponential function to the data array and utilize the exponential function to estimate whether a portion 42 represented by the most recently collected sample spectrum includes a component of thermally insulative layer 29 and/or includes a component of contaminant layer 29. In other words, control unit 18 may utilize the exponential function to determine whether to stop ablation of article 24.

Control unit 18 then may utilize at least one of the three techniques described above (cross-correlation value, change in the exponential function, or approximate rate of change of the cross-correlation value) to determine whether there is sufficient overlap between the most recently collected sample spectrum and the reference spectrum to indicate that the most recently ablated portion 42 represented by the most recently collected sample spectrum includes a component of thermally insulative layer 29 and/or includes a component of contaminant layer 29. When control unit 18 determines that there is not sufficient overlap between the most recent sample spectrum and the reference spectrum, control unit 18 returns to step (54) to ablate another portion 42 of article 24.

However, when control unit 18 determines that there is sufficient overlap between the reference spectrum and the sample spectrum, control unit 18 may proceed to stop ablation of article 42 (62). As described with reference to FIG. 7, in some embodiments, control unit 18 may optionally cause energy source 12 to output a beam of electromagnetic energy 38 at least one additional time to ensure that contaminant layer 30 has been fully removed to form a hollow (not shown in FIG. 1A or 1B) extending to thermally insulative layer 29 or is not present on thermally insulative layer 29. The number of additional pulses of energy 38 may be stored in memory in control unit 18 and may be generated automatically upon determination that the reference spectrum and sample spectrum overlaps sufficiently (84). In other embodiments, the number of additional pulses may be input by a user via a user interface and control unit 18 may generate an instruction to energy source 32 based on the input by the user.

Figure 4:
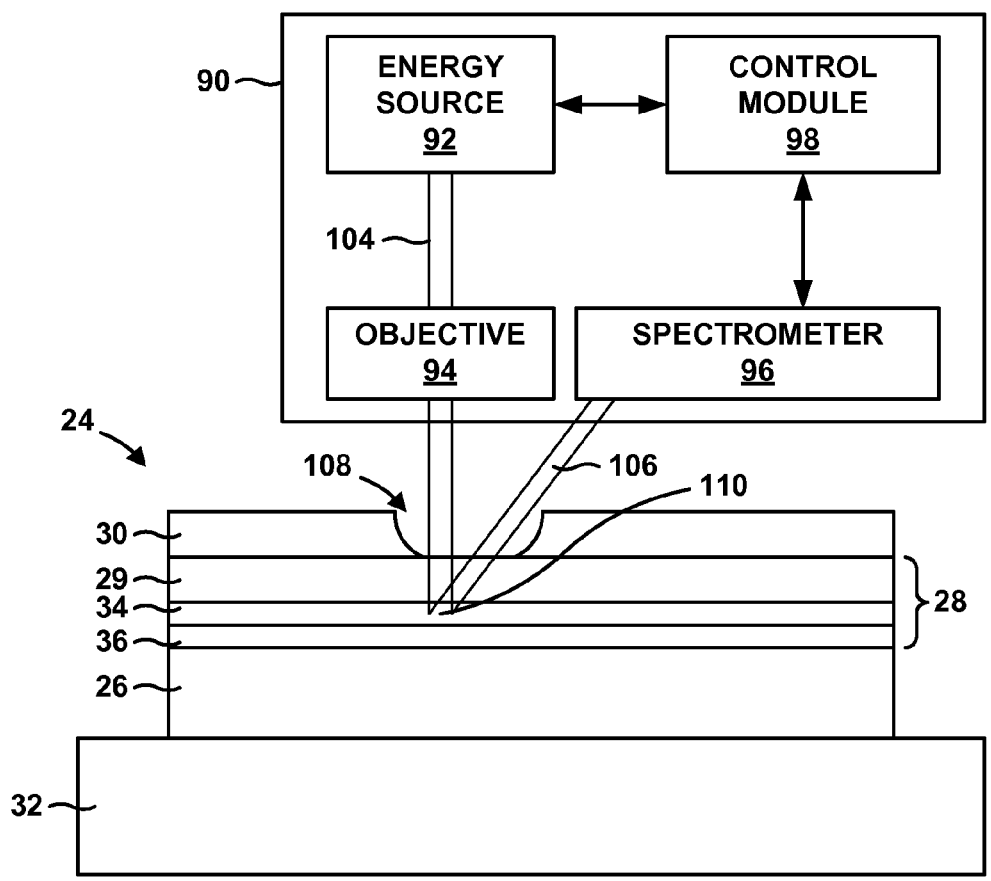
FIG. 4 is a conceptual diagram of an exemplary system for performing a photo luminescence piezo spectroscopy (PLPS) stress measurement on an article coated with a thermal barrier coating.

Once a portion of contaminant layer 30 has been removed to form a hollow extending to thermally insulative layer 29 or it has been determined that a contaminant layer 30 is not present on a portion thermally insulative layer 29, a spectroscopic technique may be utilized to analyze TBC 28. For example, photo luminescence piezo-spectroscopy (PLPS) may be used to measure residual stress in TGO 34 and estimate remaining life of TBC 28. FIG. 4 is a conceptual diagram of an exemplary PLPS system 90 that may be used to determine residual stress of a thermal barrier coating 28. PLPS system 90 may include an energy source 92, an objective lens 94, a spectrometer 96, and a control unit 98. PLPS system 90 also includes stage 32 to which article 24 is coupled.

Although the current disclosure describes PLPS, LIBS system 10 may be used to determine that a contaminant layer 30 is not present on a portion of thermally insulative layer 29 or to ablate a portion of a contaminant layer 30 in preparation for other techniques, such as, for example, laser-induced fluorescence (to measure chemical composition or temperature), Raman spectroscopy, surface-enhanced Raman spectroscopy, or the like. In fact, LIBS system 10 may be useful for ablating a portion of contaminant layer 30 in preparation for any measurement technique applied to a sample that potentially includes a contaminant layer 30.

Energy source 92 may be, for example, a laser that outputs electromagnetic energy of sufficient power and an appropriate wavelength to cause a species in TGO 29, such as, for example, a Cr atom or ion, to fluoresce when exposed to a beam of electromagnetic energy 104 output by energy source 92. Beam 104 may be substantially continuous, or may comprise a plurality of pulses. In some examples, energy source 92 may output a beam 104 having, a power of approximately 0.05 watts and a wavelength of approximately 514 nm. In other examples, energy source 92 may output a beam 104 having a wavelength of approximately 355 nm, approximately 532 nm, or approximately 1064 nm. Exemplary lasers include, but are not limited to, a Nd:YAG laser, an Excimer laser, an argon ion laser, or the like. Other laser types and wavelengths may also be used, depending on the measurement technique that is used.

Energy source 92 may output a beam 104 that is focused in or proximate to TGO 34 by objective lens 94. In some embodiments, system 90 may include a mirror or other optical element in addition to or instead of objective lens 94 to focus beam 104. Objective lens 94 may be translatable in at least one dimension to move the focal point 110 of beam 104 relative to article 24. In other embodiments, as described above, stage 32 may be translatable or rotatable in at least one dimension to move article 24 relative to objective lens 94, or each of lens 94 and stage 32 may be movable in at least one dimension to position article 32 relative to objective lens 94.

In other embodiments, PLPS system 90 may not include an objective lens 94 and energy source 92 may output electromagnetic energy that is unfocused and illuminates a relatively large area of contaminant layer 30, which includes hollow 108. Alternatively, energy source 92 may output a beam of electromagnetic energy 104 that is directed to article 24 by an optical fiber.

When a beam of electromagnetic energy 104 of sufficient power and appropriate wavelength is focused in or proximate to TGO 34, a species in TGO 34 may absorb the energy 84 and fluoresce. For example, Cr ions present in TGO 34 may fluoresce when exposed to electromagnetic energy 104 having a wavelength of approximately 532 nm or approximately 514 nm. The frequency of the fluoresced light 106 by the species in TGO 34 may be indicative of residual stress in TGO 34. Fluoresced light 106 may be directed to a spectrometer 96 by a lens, optical cable, or the like.

Spectrometer 96 may include a monochromator or polychromator that separates fluoresced light 106 into its component frequencies. For example, spectrometer 96 may include a fixed grating chromator that diffracts fluoresced light 106 according to its component frequencies in either one or two dimensions. Fluoresced light 106 is then directed onto a CCD or photomultiplier to collect a spectrum of frequencies of which fluoresced light 106 is comprised. Spectrometer 96 generates a voltage or current signal that is transmitted to control unit 98.

Control unit 98 controls operation of PLPS system 90, including energy source 92, objective lens 94, spectrometer 96, and stage 32. Additionally, control unit 98 may present a user interface that allows a user to interact with and control aspects of the operation of PLPS system 90. In some embodiments, control unit 98 may be a general computing device, such as a desktop computer, laptop computer, or the like executing on one or more microprocessors software stored in memory. In other embodiments, control unit 98 may be a special purpose computing device designed to interface only with PLPS system 90.

In some embodiments, control unit 98 may include software and hardware for interacting with a user, e.g., for receiving input from a user and outputting information to the user. For example, a user may change operational parameters of energy source 92, spectrometer 96, or positioning of objective lens 94 relative to stage 32. A user also may interact with a user interface provided by control unit 98 to manipulate and analyze data collected by spectrometer 96. During these processes, control unit 98 may present the user with user interface screens for interacting with PLPS system 90. The user may interact with the user interface presented by control unit 98 via input devices such as a keyboard, a touchscreen, a mouse, a microphone, or the like. Control unit 98 may output user interface screens for presentation to a user on, for example, an LCD screen, an LED array, a CRT screen, or a touchscreen display.

Control unit 98 may store control logic in memory that, in response to input received from a user via a user interface, directs the operation of PLPS system 90, including energy source 92, stage 32, and/or spectrometer 96. For example, control unit 98 may store software instructions in memory that, when executed, provide control logic for communicating commands to energy source 92 that specify an energy output (e.g., pulse energy, pulse power, pulse length, pulse number, beam duration, or the like), to objective lens 94 and stage 32 that specify a relative position between objective lens 94 and stage 32, and to spectrometer 96 that specifies bandwidth of the spectrum to be collected. In addition, control unit 98 may store software instructions in memory that provide commands to request and receive spectral data from spectrometer 96 during or upon completion of a PLPS process.

Control unit 98 may also store software instructions in memory that provide commands that are used to analyze the spectral data collected during the PLPS process. For example, control unit 98 may store software instructions that include a standard curve comprised of PLPS measurements performed on samples having a known residual stress in TGO 34 or an algorithm for determining residual stress in TGO 34 based on previous experiments on samples with known stresses in TGO 34. Additionally, in some embodiments, control unit 98 may store software instructions in memory that are used to process the spectral data received from spectrometer 96, such as, for example, to deconvolute overlapping peaks in the PLPS spectra.

Figure 5:
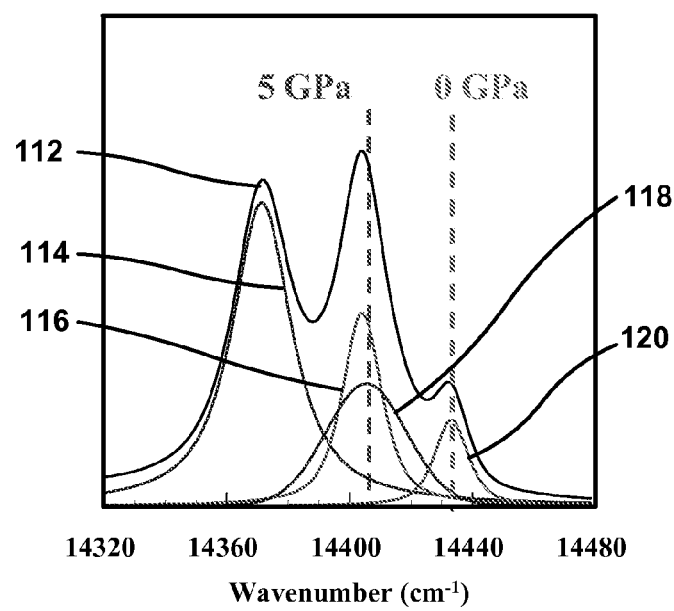
FIG. 5 is a spectral diagram of an exemplary photo luminescence piezo spectroscopy (PLPS) spectrum.

FIG. 5 is a spectral diagram that illustrates an example of a PLPS spectrum. The diagram shown in FIG. 5 includes a bimodal stress distribution, in which some of the TGO 34 is cracked and has substantially zero residual stress and some of the TGO 34 is intact and has a residual stress of approximately 5 GPa. The PLPS spectra comprises a combined curve 112, which is the spectrum of the fluoresced light 104. Control unit 98 has executed a software algorithm that has deconvoluted the fluorescence peaks 114 and 118 correlating to the portion of the TGO 34 that has a residual stress of approximately 5 GPa from the fluorescence peaks 116 and 120 corresponding to the portion of the TGO that has substantially no residual stress. Further, control unit 98 has separated peak R1 112 from peak R2 118 for the portion of the curve corresponding to the TGO 34 having a residual stress of approximately 5 GPa. Similarly, control unit 98 has separated peak R1 116 from peak R2 120 for the portion of the curve corresponding to the TGO 34 having a residual stress of approximately 0 GPa.

To estimate remaining life of a TBC 28 based on measured fluorescence frequency in TGO 34 of an unknown sample, the relationship between fluorescence frequency shift and residual stress, and between residual stress and remaining life, must first be determined based on known samples. For example, to determine the relationship between fluorescence frequency and residual stress in TGO 34, a series of samples of similar composition to TGO 34 may be exposed to known stresses, such as known compressive stresses. The samples then undergo PLPS measurements, and the frequency of the fluoresced light may be measured for each sample having a known residual stress. This may be used to form a standard curve of residual stress versus fluorescence frequency. In some embodiments, the frequency of the fluoresced light may be converted to a wavenumber. Additionally, the standard curve may be reduced to an equation of a line of best fit, which may be stored in memory in control unit 98.

Once the relationship between fluorescence frequency or wavenumber and residual stress is known, the relationship between residual stress and remaining life may be determined. To determine this relationship, a set of samples including substrates coated with TBCs 28 may be exposed to a series of heat treatment cycles in order to thermally stress the component and generate stresses on the TBCs 28, e.g., at the interfaces between thermally insulative layer 29, TGO 34 and bond coat 36. The samples are periodically tested via PLPS to determine the residual stress in TGO 34 and the thermal cycle number at which the PLPS measurement was made is recorded. Thermal cycling of the samples continues until each sample has failed, which may be defined as spallation of a portion of the TBC 28 from the substrate 26 of the sample. The remaining life is calculated by dividing the thermal cycle at which a respective PLPS measurement was made by the total number of thermal cycles the sample experienced prior to failure. A standard curve of remaining life versus residual stress may be generated from data points for each of the samples, and an equation of a line of best fit may be calculated from the standard curve. This equation may also be stored in memory in control unit 98. The equations for converting the frequency of the fluoresced light to residual stress and residual stress to remaining life then may be utilized by control unit 98 to estimate remaining life of an unknown sample.

In some embodiments, other characteristics of the fluoresced light 106 may be utilized by control unit 98 in addition to or as an alternative to residual stress to estimate remaining life of TBC 28. For example, at least one of full width of the peak at half maximum of the peak (either the R1 peak or the R2 peak), spacing between the R1 and R2 peaks, a Gaussian/Lorenzian ratio of the peak fit, a ratio of bimodal to unimodal spectra collected, or standard deviation of the stress for multiple measurements may be used to estimate remaining life of TBC 28.

In some embodiments, a single system may be used to perform LIBS to remove a portion of a contaminant layer 30 from an article 24 and perform a PLPS stress measurement on a TGO 34 of the article 24. FIG. 6 illustrates one such system. LIBS/PLPS system 130 includes an energy source 132, an objective lens 134, a control unit 138, a first spectrometer 144, a second spectrometer 146 and a beamsplitter 136. LIBS/PLPS system 130 also includes a stage 32, to which an article 24 is coupled.

Energy source 132 may be capable of outputting electromagnetic energy at a first energy setting and a second energy setting. For example, energy source 132 may be a laser capable of emitting a beam of electromagnetic energy 142, which may correspond to a beam 38 of sufficient intensity to ablate a portion 42 of article 24 (e.g., contaminant layer 30 and/or thermally insulative layer 29; FIGS. 1A and 1B) or a beam 104 of sufficient power and an appropriate wavelength to cause a species in TGO 34, such as, for example, a Cr atom or ion, to fluoresce when exposed to the beam 104 (FIG. 4). The power required to induce fluorescence in a species in TGO 34 may be significantly lower than the power required to ablate portion 42. In some embodiments, energy source 132 may comprise a Nd:YAG (Nd-doped yttrium aluminium garnet; Nd:$Y_3Al_5O_{12}$) laser that outputs electromagnetic energy with a nominal wavelength of approximately 355 nm, approximately 532 nm, or approximately 1064 nm. In other embodiments, energy source 132 may comprise a different type of laser, such as an Excimer laser, an argon ion laser, or the like, may output electromagnetic energy having a different nominal wavelength (such as 514 nm), or both.

In some embodiments, energy source 132 may emit beam 142 as a single pulse or a series of pulses. For example, each pulse may have a pulse length between approximately 10 nanoseconds (ns) and approximately 20 ns. In other embodiments energy source 132 may emit beam 142 as a pulse or series of pulses having a pulse length on the order of femtoseconds, picoseconds, or microseconds. In some embodiments, energy source 132 may also be capable of emitting beam 142 as a substantially continuous beam of energy.

Energy source 132 may emit beam 142 with pulses of a sufficient intensity to ablate portion 42, which may include a portion of contaminant layer 30 and/or a portion of thermally insulative layer 29 (FIG. 1B). The effective pulse intensity may be a function of the pulse length, pulse energy, and focusing optics, including objective lens 134. In some examples, the pulse energy may be greater than 100 mJ. In other examples, the pulse energy may be between approximately 5 mJ and approximately 75 mJ. Additionally, energy source 132 may emit beam 142 having a lower power, such as approximately 0.05 W, to induce fluorescence of a species, such as a Cr atom or ion, in TGO 34.

Energy source 132 emits beam 142 through objective lens 134, which focuses beam 142 proximate to article 24. Objective lens 134 may focus beam 142 proximate to outer surface 46 of contaminant layer 30 or another location within contaminant layer 30 or thermally insulative layer 29. Objective lens 134 also may focus beam 142 to a focal point 110 within TGO 34 (FIG. 4). Objective lens 134 may focus beam 142 to a relatively small volume in order to increase a pulse intensity of the beam 142. In some embodiments, objective lens 134 may be translatable in one, two, or three dimensions to control a location at which beam 142 is focused.

In some embodiments, article 24 may be mounted or positioned on a movable stage 32, which may be used in conjunction with objective lens 134 to focus beam 142 at a desired position relative to article 24, e.g., at a position on or within contaminant layer 30 or a position within TGO 34. Stage 32 may be translatable in one, two, or three dimensions.

In some embodiments, stage 32 and objective lens 134 may operate in conjunction to position article 24 relative to objective lens 134. For example, stage 32 may be translatable in two dimensions (e.g., an x-y plane in the coordinate system shown in FIG. 1A) and objective 134 may be translatable in one dimension (e.g., the z-axis in FIG. 1A). In other embodiments, each of objective lens 134 and stage 32 may be translatable in three dimensions and may work in conjunction to position the focal point of beam 142 relative to article 24. For example, stage 32 may provide relatively coarse positioning of article 32, while objective lens 134 provides relatively more precise positioning of the focal point of beam 142. As another example, stage 32 may provide relatively slow positioning of article 24 relative to beam 142, while objective lens 134 provides relatively faster positioning of beam 142 with respect to article 24. In some embodiments, one or both of objective lens 134 or stage 32 may move according to another coordinate system. For example, one or both of objective lens 134 or stage 32 may be positioned according to a polar coordinate system or a spherical coordinate system. In other words, positioning of one or both of objective lens 134 or stage 32 may include rotational positioning and not only linear positioning.

PLPS/LIBS system 130 also includes a first spectrometer 144 and a second spectrometer 146, to which respective portions 140a, 140b of emitted electromagnetic radiation 140 are directed by beam splitter 136. Beam splitter 136 may include, for example, two triangular glass prisms glued at their base, which transmit a first portion 140a of incident emitted electromagnetic radiation 140 and reflect the second portion 140b of incident emitted electromagnetic radiation 140. Beam splitter 136 may also comprise a polarizing beam splitter, a half-silvered mirror, or the like. In other embodiments, system 130 may not include beam splitter 136, but may instead include a mirror or other optical element that is movable to direct emitted electromagnetic energy 140 to a respective one of first spectrometer 144 or second spectrometer 146. In some embodiments, system 130 may include only a single spectrometer, which may be used during both the LIBS process and PLPS measurement, and system 130 may not include any optical element to direct energy 140 along one of two optical paths.

First spectrometer 144 and second spectrometer 146 may be utilized for detecting wavelengths of electromagnetic energy 40 emitted by ablated portion 42 (FIGS. 1A and 1B) and fluoresced light 106 emitted by a species in TGO 34 (FIG. 4). In this way, emitted electromagnetic energy 140 may at different times include either emitted electromagnetic energy 40 or fluoresced light 106. System 130 may include first spectrometer 144 and second spectrometer 146 due to different requirements for detection of electromagnetic energy 40 and fluoresced light 106. For example, a spectrometer with a fairly low spectral resolution may be utilized for detecting electromagnetic energy 40, while detection of fluoresced light 106 during a PLPS measurement may require a finer spectral resolution. However, in some embodiments, system 130 may include a single spectrometer that is used for detecting both emitted electromagnetic energy 40 and fluoresced light 106.

Each of first spectrometer 144 and second spectrometer 146 may or may not include a shutter 20 and a charge coupled device (CCD) 22 (FIG. 1A). Because first spectrometer 144 may be used to detect and measure emitted electromagnetic energy 40, first spectrometer 144 may include a shutter 20 to prevent or allow emitted electromagnetic energy 40 to illuminate CCD 22. For example, as described above, following ablation, portion 42 may emit a substantially continuous spectrum of electromagnetic energy, which may not be useful in determining the composition of portion 42. A shutter 20 in first spectrometer 144 may be closed at this time to prevent the substantially continuous electromagnetic energy from reaching CCD 22. After a time delay, the shutter 20 may open to allow electromagnetic energy 40, which now includes distinct wavelength peaks indicative of elements present in energy 40, to reach and be detected by the CCD 22 in first spectrometer 144. In this way, first spectrometer 144 may be used to collect a spectrum of wavelengths of which emitted electromagnetic energy 40 is comprised.

In some embodiments, at least one of first spectrometer 144 or second spectrometer 146 may include a detector other than a CCD 22 for detecting emitted electromagnetic energy 140$a$, 140$b$. For example, second spectrometer 146 may include a photomultiplier in combination with a filter or set of filters that separate wavelengths of the emitted electromagnetic energy 140$b$ and pass a small set of wavelengths to the photomultiplier.

In some embodiments, at least one of first spectrometer 144 and second spectrometer 146 may include a fixed grating chromator, which disperses emitted electromagnetic energy 140$a$ or 140$b$ in one or two dimensions along a CCD 22 or another detector according to the frequency of photons in electromagnetic energy 140$a$ or 140$b$.

Figure 6:
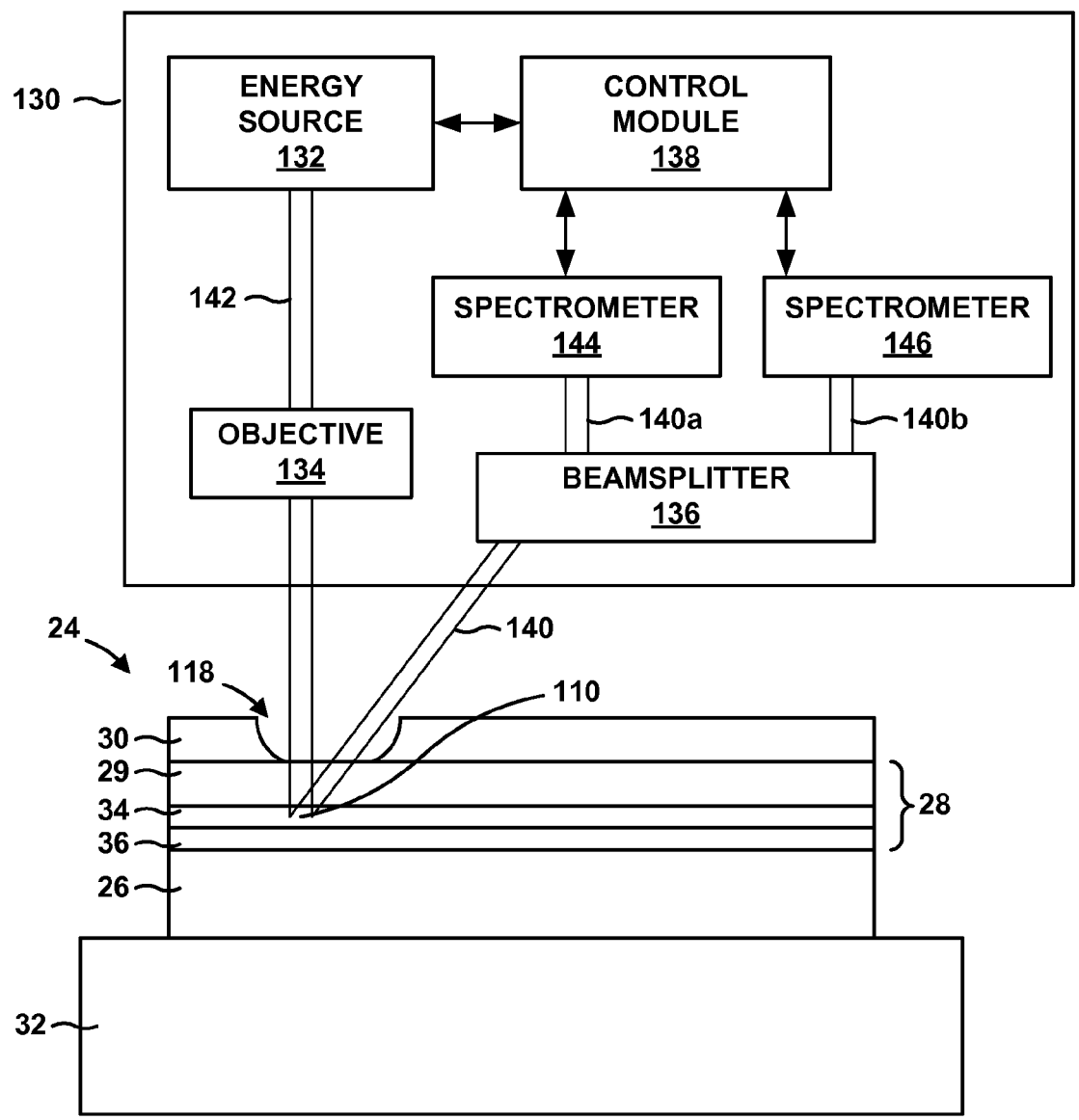
FIG. 6 is a conceptual diagram of an exemplary combined laser induced breakdown spectroscopy (LIBS) and photo luminescence piezo spectroscopy (PLPS) system.

Although not shown in FIG. 6, in some embodiments, beam splitter 136 may be coupled to an optical fiber (not shown) that accepts electromagnetic energy 140 and directs energy 140 to beam splitter 136. In some embodiments, the optical fiber may act as a wavelength filter or a spatial filter which permits only a certain set of wavelengths or energy 140 emitted from a certain spatial location to pass to beam splitter 136.

LIBS/PLPS system 130 further includes a control unit 138, which controls operation of energy source 132, objective 134, first spectrometer 144, second spectrometer 146 and stage 32. Additionally, control unit 138 may present a user interface that allows a user to interact with and control aspects of the operation of LIBS/PLPS system 130. In some embodiments, control unit 138 may be a general computing device, such as a desktop computer, laptop computer, or the like executing on one or more microprocessors software stored in memory. In other embodiments, control unit 138 may be a special purpose computing device designed to interface only with LIBS/PLPS system 130.

In some embodiments, control unit 138 may include software and hardware for interacting with a user, e.g., for receiving input from a user and from outputting information to the user. For example, a user may change operational parameters of energy source 132, first spectrometer 144, second spectrometer 146, or positioning of objective lens 134 relative to stage 32. A user also may interact with a user interface provided by control unit 138 to manipulate and analyze data collected by at least one of first spectrometer 144 and second spectrometer 146. During these processes, control unit 138 may present the user with user interface screens for interacting with LIBS/PLPS system 130. The user may interact with the user interface presented by control unit 138 via input devices such as a keyboard, a touchscreen, a mouse, a microphone, or the like. Control unit 138 may output user interface screens for presentation to a user on, for example, an LCD screen, an LED array, a CRT screen, or a touchscreen display.

Control unit 138 may store control logic in memory that, in response to input received from a user via a user interface, directs the operation of LIBS/PLPS system 130, including energy source 132, stage 32, first spectrometer 144 and/or second spectrometer 146. For example, control unit 138 may store software instructions in memory that, when executed, provide control logic for communicating commands to energy source 132 that specify an energy output (e.g., pulse energy, pulse power, pulse length, pulse number), to objective lens 134 and stage 32 that specify a relative position between objective 134 and stage 32, and to first and/or second spectrometer 144 or 146 that specifies a timing for opening and closing of a shutter. In addition, control unit 138 may store software instructions in memory that provide commands to request and receive spectral data from first spectrometer 144 during or upon completion of a LIBS process or from second spectrometer 146 during or upon completion of a PLPS measurement.

Control unit 138 may also store software instructions in memory that provide commands that are used to analyze the spectral data collected during the LIBS process or the PLPS measurement. For example, control unit 138 may store software instructions that include exemplary LIBS spectra or characteristic emission wavelengths for a plurality of exemplary elements or TBC compositions, in order to provide reference spectra or emission wavelengths to which the collected LIBS spectra may be compared (for example, in a cross-correlation technique). As other examples, control unit 138 may store software instructions that include a standard curve comprised of PLPS measurements performed on samples having a known residual stress in TGO 34 or an algorithm for determining residual stress in TGO 34 based on previous experiments on samples with known stresses in TGO 34. Additionally, in some embodiments, control unit 138 may store software instructions in memory that are used to process the spectral data received from second spectrometer 146, such as, for example, to deconvolute overlapping peaks in the PLPS spectra.

Figure 7:
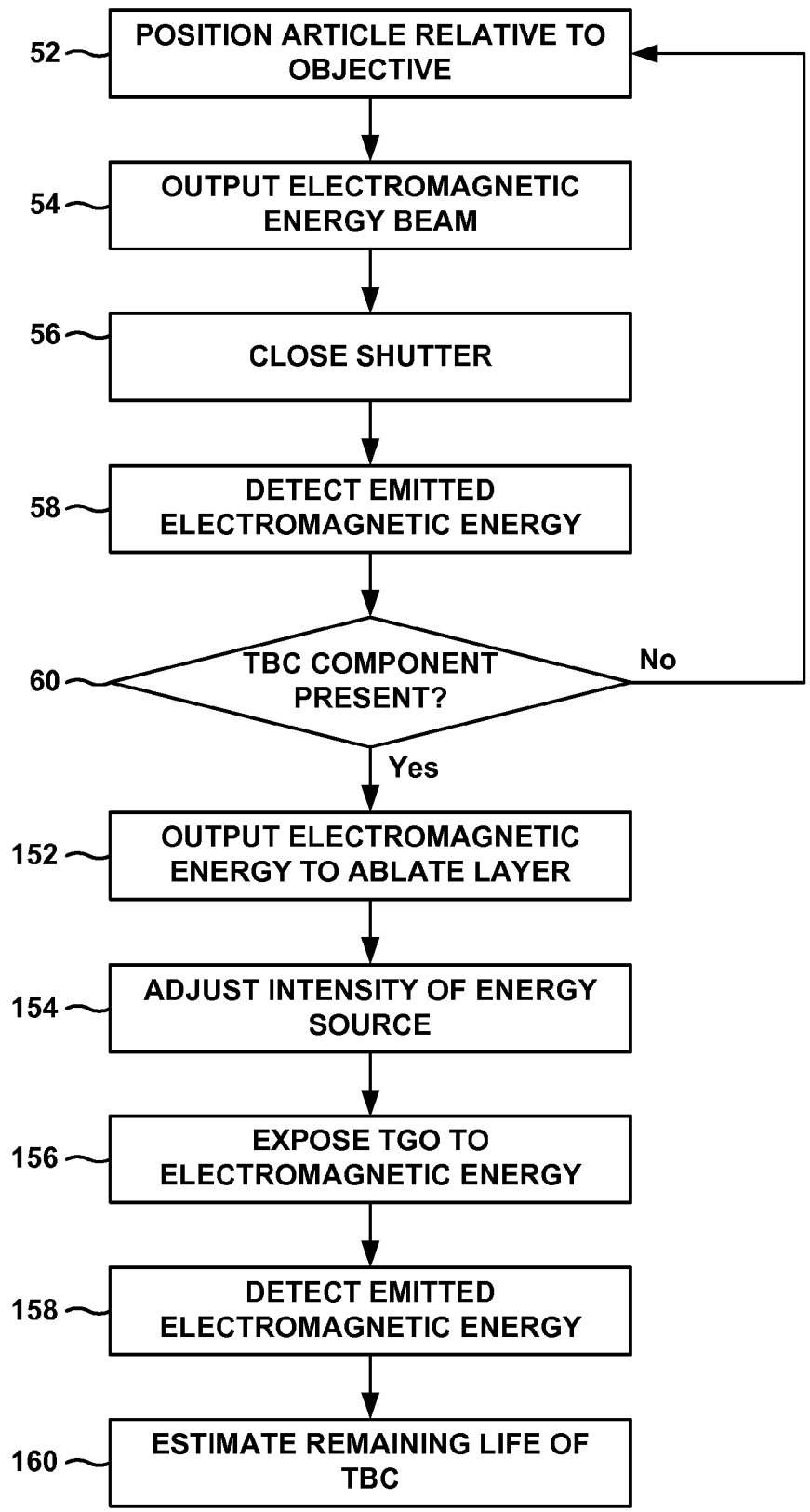
FIG. 7 is a flow diagram of an exemplary technique for determining whether a portion of an article includes a component of a thermal barrier coating (TBC) and, if a contaminant layer is present on the TBC, removing a portion of the contaminant layer from the TBC prior to performing a photo luminescence piezo spectroscopy (PLPS) stress measurement on the article.

FIG. 7 is a flow diagram of an example of a technique for determining whether a portion of an article includes a component of a TBC 28 and, if a component of a contaminant layer 30 is present the portion, removing a subsequent portion of the contaminant layer 30 using LIBS. The technique described with reference to FIG. 7 further includes performing a PLPS measurement to estimate remaining life of the TBC 28. FIG. 7 will be described with reference to the LIBS/PLPS system 130 of FIG. 6. Nevertheless, in other embodiments, the technique described in FIG. 7 may be performed using separate LIBS and PLPS systems, such as those described with reference to FIGS. 1A, 1B and 4.

As described above with respect to FIG. 2, article 24 is positioned relative to objective lens 134 (and, ultimately, a path of beam 142) by moving at least one of stage 32 or objective lens 134 (52). In various embodiments, control unit 138, a user, or a combination of control unit 138 and a user may control the positioning of article 24 relative to objective lens 134.

Once article 24 is positioned relative to objective lens 134 such that beam of electromagnetic energy 142 is focused proximate to a surface of contaminant layer 30 and/or TBC 28 (e.g., thermally insulative layer 29), control unit 138 causes energy source 132 to output beam 142 in a single pulse or a set of pulses (54). Control unit 138 may automatically (e.g., without intervention of a user) cause energy source 132 to output beam 142 once article 24 is positioned relative to objective lens 134 such that beam 142 is focused proximate to a surface of contaminant layer 30 and/or TBC 28. In other embodiments, a user may enter a command via a user interface that causes control unit 138 to cause energy source 132 to output beam 142.

As described above, portion 42 may include a portion of contaminant layer 30 and/or a portion of thermally insulative layer 29. Ablation of portion 42 may occur when beam 142 heats portion 42 to a sufficient temperature to vaporize portion 42 and eject portion 42 from contaminant layer 30 and/or TBC 28. Portion 42 may form a plasma above the surface of article 24 and emit electromagnetic energy in a substantially continuous spectrum for a time after beam 142 ceases. This substantially continuous spectrum may not be useful for determining the composition of portion 42, and a shutter of first spectrometer 144 may be closed during this time to prevent the emitted electromagnetic energy 140 comprising the substantially continuous spectrum from reaching the CCD (56). As the plasma cools, the free electrons in the plasma may rebind to the atomic elemental components of portion 42. During this process, the free electrons emit electromagnetic energy 140 comprising strong peaks at certain wavelengths corresponding to elements in portion 42 and the atoms emit electromagnetic energy 140 comprising strong atomic transitions within the atom. At this time, the shutter of first spectrometer 144 may be open to allow first portion 140a of emitted electromagnetic energy 140 including the strong peaks to reach the CCD. The CCD detects the emitted electromagnetic energy 140 (58), and may convert the emitted electromagnetic energy 140 to a signal, such as, for example, a voltage or current signal, which is transmitted to control unit 138.

Control unit 138 receives the signal from first spectrometer 144 and analyzes the signal to determine whether a component of TBC 28 (e.g., thermally insulative layer 29) is present in the ablated portion 42 (60). In some embodiments, control unit 138 may automatically determine whether a component of thermally insulative layer 29 is present in portion 42. For example, control unit 138 may automatically apply an algorithm, such as cross-correlation, to the signal received from first spectrometer 144 to determine is a component of thermally insulative layer 29 is present in portion 42. In other embodiments, control unit 138 may display the spectrum detected by first spectrometer 144 to a user in graphical, tabular or numerical form and the user may make a determination of whether portion 42 contains any elements present in thermally insulative layer 29.

In some embodiments, when control unit 138 or a user determines an element from thermally insulative layer 29 is not present in portion 42, this may indicate that a contaminant layer 30 is present on TBC 28. The technique then may return to step (52) and article 24 may be repositioned relative to objective lens 134 to reposition the focal point of beam 142 to a new location proximate to a surface of contaminant layer 30. In other embodiments, article 24 may not need to be repositioned relative to objective lens 134, and the technique may return directly to step (54). Regardless of whether the technique returns first to step (52) or proceeds directly to step (54), control unit 138 may automatically or under control of the user cause energy source 132 to output a beam of electromagnetic energy 142 (54). Beam 142 may again comprise a pulse or series of pulses of sufficient intensity to ablate a second portion of contaminant layer 30 (not shown in FIG. 7). The pulse characteristics, such as pulse energy, pulse length (duration), and pulse area may be the same or different than those used during the first iteration of step (54). The second ablated portion may be located substantially below depression 44 (FIG. 1B) formed by ablation of portion 42, and may be closer to thermally insulative layer 29 than portion 42 was. In effect, the sequential ablation of portions of contaminant layer 30 forms a hollow extending from outer surface 46 of contaminant layer 30, into layer 30, and towards thermally insulative layer 29.

The process continues through steps (56) and (58), with the CCD in first spectrometer detecting emitted electromagnetic energy 140 and outputting a voltage or current signal indicative of the emitted electromagnetic energy 140 to control unit 138.

Control unit 138 receives the signal from first spectrometer 144 and analyzes the signal to determine whether a component of TBC 28 (e.g., thermally insulative layer 29) is present in the ablated second portion (60). In some embodiments, control unit 138 may automatically determine whether a component of thermally insulative layer 29 is present in the second portion. For example, control unit 138 may automatically apply an algorithm, such as cross-correlation, to the signal received from spectrometer 138 to determine is a component of thermally insulative layer 29 is present in the second portion. In other embodiments, control unit 138 may display the spectrum detected by first spectrometer 144 to a user in graphical, tabular or numerical form and the user may make a determination of whether the second portion contains any elements present in thermally insulative layer 29.

When control unit 138 or a user determines that the second portion does not contain an element of thermally insulative layer 29, the technique may again return to one of step (52) or step (54), and the process may repeat to remove a third ablated portion.

However, when control unit 138 or a user determines that an element of thermally insulative layer 29 is present in the ablated portion 42 (or subsequent ablated portions), this may indicate that a contaminant layer 30 is not present on thermally insulative layer 29 or that a portion of contaminant layer 30 extending substantially from outer surface 46 of contaminant layer 30 to outer surface 48 of thermally insulative layer 29 has been ablated to form a hollow 108 extending from outer surface 46 to outer surface 48. In some embodiments, control unit 138 may optionally cause energy source 132 to output a beam of electromagnetic energy 142 at least one additional time (152) to ensure that contaminant layer 30 has been fully removed to form the hollow 108 extending to thermally insulative layer 29 or is not present on thermally insulative layer 29. The number of additional pulses of energy 142 may be stored in memory in control unit 138 and may be generated automatically upon detection of an element of thermally insulative layer 29 in ablated portion 42. In other embodiments, the number of additional pulses may be input by a user via a user interface and control unit 138 may generate an instruction to energy source 132 based on the input by the user.

Upon determination that a contaminant layer 30 is not present on thermally insulative layer 29 or formation of hollow 108 extending through contaminant layer 30 to thermally insulative layer 29, LIBS/PLPS system 130 may be used to perform a PLPS measurement on TGO 34 located below hollow 108 (in a direction normal to the surface of substrate 26). Control unit 138 first causes energy source 132 to adjust its output intensity (154). Control unit 138 may cause energy source 132 to lengthen the pulse length (duration) of electromagnetic energy 142, lower the pulse power or energy of electromagnetic energy 142, or both, to lower the effective intensity of energy 142. For example, control unit 138 may cause energy source 132 to output electromagnetic energy 142 with a power of approximately 0.05 watts.

Control unit 138 then may cause at least one of stage 32 or objective lens 134 to move to position the focal point 110 of electromagnetic energy 142 to be in or proximate to TGO 34, as shown in FIG. 6, and may cause energy source 132 to output a beam of electromagnetic energy 142 (156).

When a beam of electromagnetic energy 142 of sufficient power and appropriate wavelength is focused in or proximate to TGO 34, a species in TGO 34 may absorb the energy 142 and fluoresce. For example, Cr ions present in TGO 34 may fluoresce when exposed to electromagnetic energy 142 having a wavelength of approximately 532 nm or approximately 514 nm. The frequency of the emitted electromagnetic energy 140 fluoresced by the species in TGO 34 may be indicative of residual stress in TGO 34. A second portion 140b of emitted electromagnetic energy 140 may be directed to second spectrometer 146 by a lens, optical cable, mirror, beam splitter 136 or the like.

Second spectrometer 146 may separate second portion 140b of emitted electromagnetic energy 140 into its component frequencies. For example, second spectrometer 146 may include a fixed grating chromator that diffracts second portion 140b according to its component frequencies in either one or two dimensions. Second portion 140b is then directed onto a CCD or photomultiplier to detect a spectrum of frequencies of which emitted electromagnetic energy 140 is comprised (158). Second spectrometer 146 generates a voltage or current signal that is transmitted to control unit 138 for further processing.

Control unit 138 may analyze the spectral data received from second spectrometer 146 using algorithms stored in memory to estimate remaining life of TBC 28 (160). For example, control unit 138 may estimate remaining life of TBC 28 based on the relationship between fluorescence frequency shift and residual stress, and the relationship between residual stress and remaining life. These relationships may be determined as described above with respect to FIG. 4, and may be stored in memory in control unit 138.

In some embodiments, characteristics other than residual stress may be calculated from the spectrum of second portion 140b of emitted electromagnetic energy 140 and may be utilized by control unit 138 in addition to or as an alternative to residual stress to estimate remaining life of TBC 28. For example, at least one of full width of the peak at half maximum of the peak (either the R1 peak or the R2 peak), spacing between the R1 and R2 peaks, a Gaussian/Lorenzian ratio of the peak fit, a ratio of bimodal to unimodal spectra collected, or standard deviation of the stress for multiple measurements may be used to estimate remaining life of TBC 28.

Once the remaining life of TBC 28 has been estimated, a determination of whether to continue use of article 24 or remove article 24 from service may be made. In this way, LIBS/PLPS system 130 may be used to make a non-destructive estimation of remaining life of article 24.

The techniques described in this disclosure, including those attributed to control unit 18, 98, or 138, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied a general purpose or purpose-built computing device. The term "processor" or "processing circuitry" may generally refer to any of the foregoing logic circuitry, alone or in combination with other logic circuitry, or any other equivalent circuitry.

Such hardware, software, firmware, or combinations thereof may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware and/or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), magnetoresistive random access memory (MRAM), FLASH memory, magnetic data storage media, optical data storage media, or the like. The instructions may be executed to support one or more aspects of the functionality described in this disclosure.

EXAMPLES

Examples 1-4

FIGS. 8A-8D show the results of removal of portions of a contaminant layer from a TBC using a tripled Nd:YAG laser emitting laser radiation with a wavelength of 355 nm. The pulse frequency of 10 Hz and single shot energy of 65 mJ were held constant while the spot size and total number of pulses were varied. The number of pulses was varied such that the total energy per unit area delivered to the target area remained constant based on spot size (laser intensity). The laser spot size was doubled for each subsequent spot, so the laser spot size used to ablate the contaminant portion in FIG. 8B (0.0058 cm$^2$) was twice as large as the laser spot size used in FIG. 8A (0.0029 cm$^2$). Similarly, the laser spot size used to ablate the contaminant portion in FIG. 8C (0.0117 cm$^2$) was twice as large as the laser spot size used in FIG. 8B, and the laser spot size used to ablate the contaminant portion in FIG. 8D (0.0233 cm$^2$) was twice as large as the laser spot size used in FIG. 8C. Additionally, the number of pulses was also doubled for each subsequent spot, so the number of pulses used in FIG. 8B (60) was double the number of pulses used in FIG. 8A (30). Similarly, the number of pulses used in FIG. 8C (120) was double the number of pulses used in FIG. 8B, and the number of pulses used in FIG. 8D (240) was double the number of pulses used in FIG. 8C.

Figures 8A, 8B, 8C, 8D:
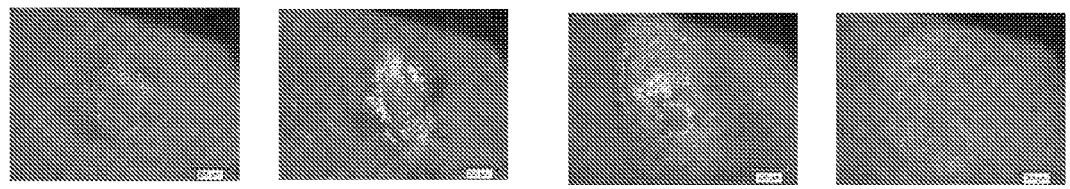
FIGS. 8A-8D are exemplary microscopy images of thermal barrier coatings having portions removed by laser ablation.
Figure 9:
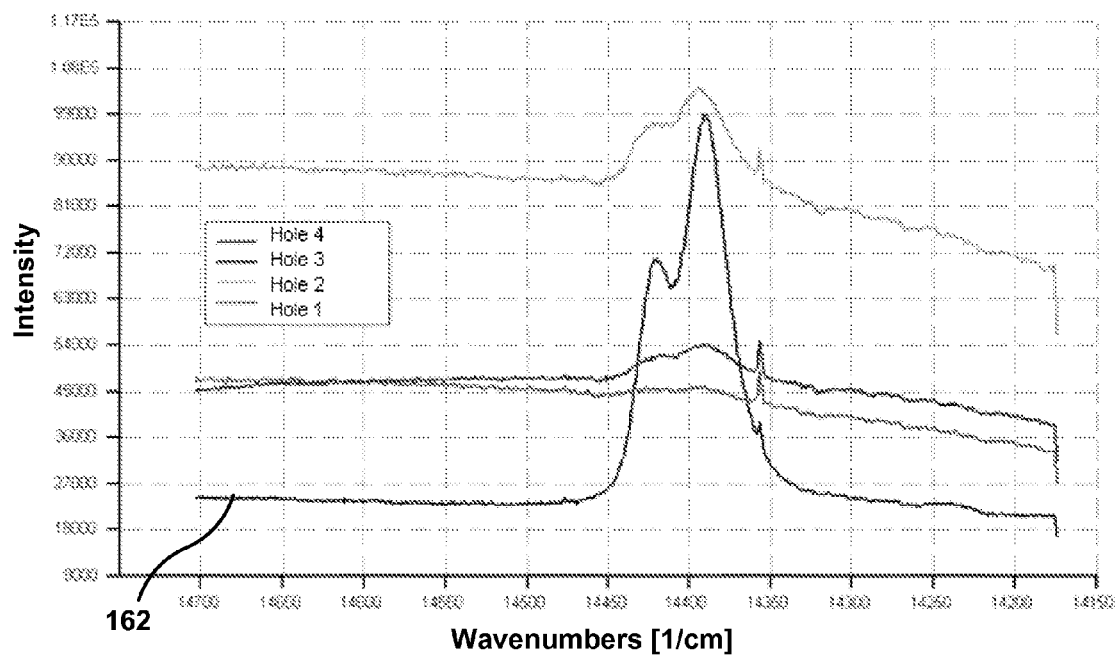
FIG. 9 is an example of a diagram showing photo luminescence piezo spectroscopy (PLPS) spectra collected from each of the portions of FIGS. 7A-7D.

After the contaminant was removed from each of the four portions, PLPS spectra were collected for each of the portions. FIG. 9 is a diagram of the PLPS spectra for each of the portions. The spectrum 162 collected from the fourth portion, corresponding to FIG. 8D, shows the expected bimodal intensity distribution and may be used to determine the stress in the TGO. As described above, the removal of the contaminant portion in FIG. 8D was accomplished using the largest laser spot size and the largest number of pulses. The results of these experiments show that laser ablation may be used to remove a contaminant layer from a TBC to allow collection of a PLPS spectrum from the TGO.

Examples 5-8

In order to determine that laser ablation of a contaminant layer does not affect the PLPS stress measurement, a study was performed on an uncontaminated turbine blade. The blade was furnace treated for five one-hour thermal cycles at approximately 1121° C. in order to initiate TGO growth and allow acquisition of PLPS spectra. Four holes were then formed by ablation of the surface of the TBC using a laser spot size of 1.7 mm (area of laser spot=2.34 mm$^2$) and a laser energy of 65 mJ with 120, 180, 240 and 280 pulses, respectively. Nine separate spectral acquisitions were made on the blade before laser ablation and 21 separate spectral acquisitions were made on the blade after production of the four separate holes. The spectra were collected from multiple locations both before and after production of the holes.

Figure 10:
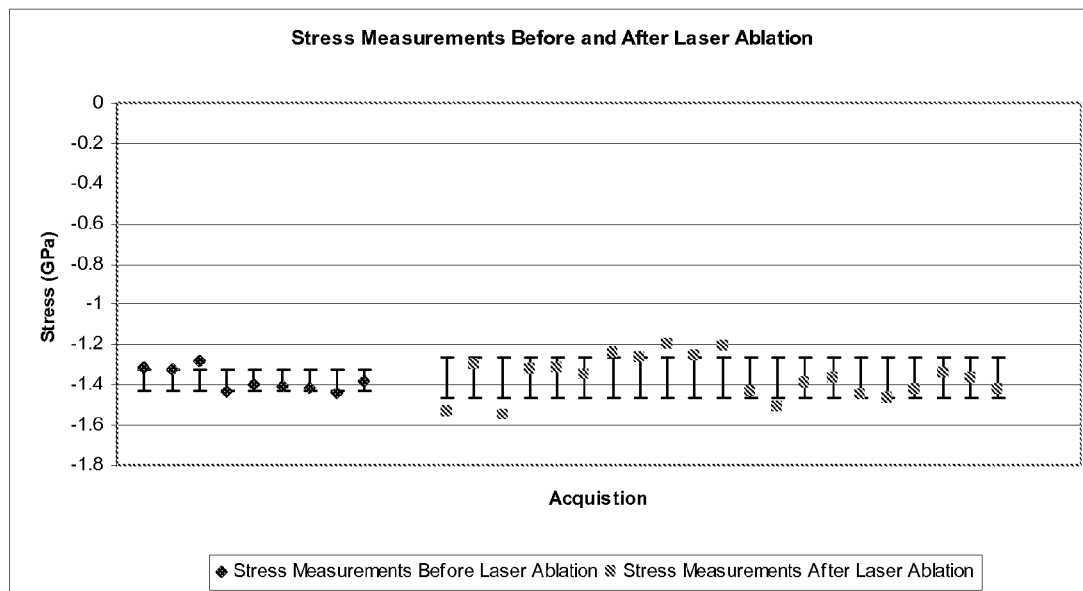
FIG. 10 is an example of a scatter diagram of a plurality of stress calculations from photo luminescence piezo spectroscopy (PLPS) spectra collected from an article coated with a thermal barrier coating before and after laser ablation.

FIG. 10 is a scatter diagram of the stress values calculated from the collected spectra. The stress values calculated from the spectra collected before laser ablation of the four holes are illustrated by diamond markers and the stress values calculated from the spectra collected after laser ablation are illustrated by square markers. The average stress value before laser ablation is approximately −1.38 GPa, and the average stress after laser ablation is approximately −1.366 GPa. This supports that the laser ablated holes within the parameter range selected do not produce altered PLPS measurements or affect the stress computation from the PLPS spectrum. Additionally, the measurements were very consistent between locations both before and after the laser ablation process.

Examples 9 and 10

Figure 11:
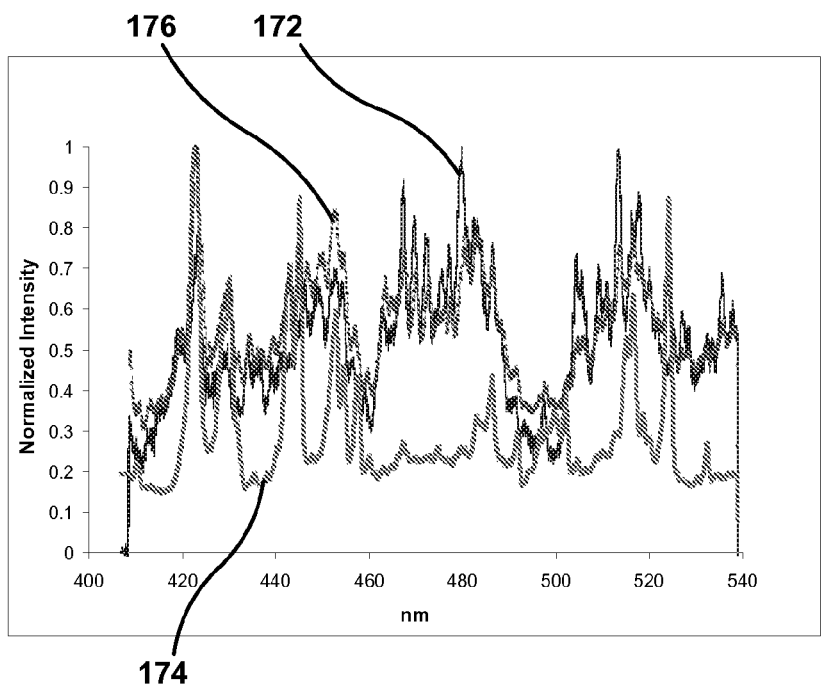
FIG. 11 is an example of a scatter diagram comparing emission spectra of a reference substrate, a sample including a contaminant after a first ablation, and the sample including the contaminant after an eighty-fifth ablation.

FIG. 11 is an example of a scatter diagram comparing emission spectrum of a reference substrate 172 comprising 6-8 wt. % yttria-stabilized zirconia, an emission spectrum of a sample including a contaminant on a 6-8 wt. % yttria-stabilized zirconia coating after a first ablation cycle 174, and an emission spectrum the sample including the contaminant on the 6-8 wt. % yttria-stabilized zirconia coating after an eighty-fifth ablation cycle 176. Each of the ablation cycles were performed by a laser outputting electromagnetic energy at a wavelength of approximately 355 nm, an energy of approximately 65 mJ, a pulse width of 20 nanoseconds, and a spot size of approximately 0.6 mm. FIG. 11 illustrates that emission spectrum 176 is more similar to emission spectrum 172 than emission spectrum 174 is similar to emission spectrum 172. In other words, emission spectrum 176 implies that the sample is more similar to the reference substrate after the eighty-fifth ablation cycle than after the first ablation cycle.

Figure 12:
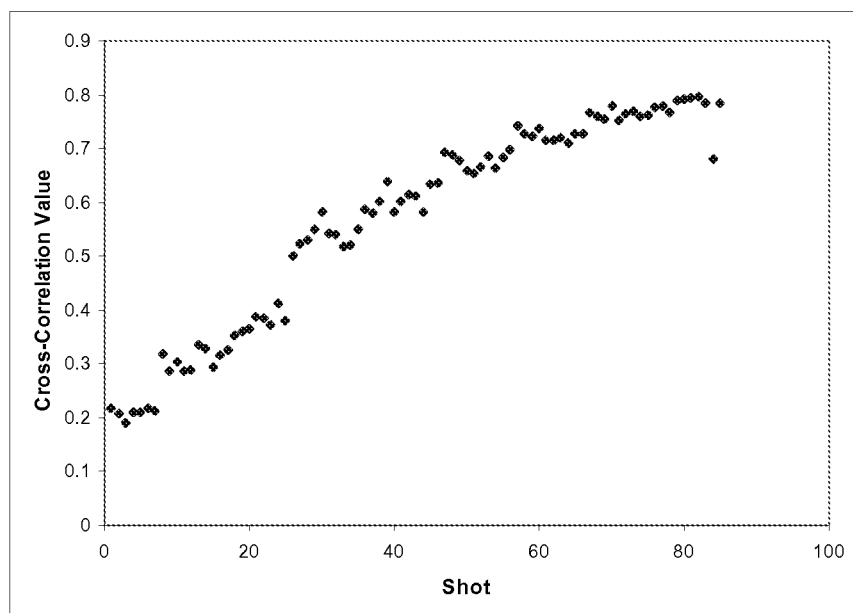
FIG. 12 is an example of a scatter diagram of cross correlation values calculated for each a plurality of ablation cycles.

FIG. 12 is an example of a scatter diagram of cross correlation values calculated for each the eighty-five ablation cycles the sample referred to in FIG. 11 underwent. FIG. 12 shows that the cross-correlation value substantially monotonically increases as the ablation cycle increases. Additionally, FIG. 12 illustrates that the cross-correlation value is approaching an asymptotic value between approximately 0.8 and approximately 0.9

Various embodiments have been described. These and other embodiments are within the scope of the following claims.

The invention claimed is:

1. A method comprising:
   outputting electromagnetic energy at a first energy setting from an energy source;
   exposing a portion of an article comprising a substrate, a thermal barrier coating comprising a thermally grown oxide on the substrate, and a thermally insulative layer on the thermally grown oxide to the first energy setting to ablate the portion of the article, wherein the portion of the article comprises a portion of the thermally insulative layer;
   collecting a spectrum of electromagnetic energy emitted by the portion of the article after ablation;
   determining, based on the collected spectrum of electromagnetic energy, that a component of the thermally insulative layer is present in the portion of the article;
   outputting electromagnetic energy at a second energy setting from the energy source, wherein the second energy setting is different than the first energy setting,
   exposing a portion of the thermally grown oxide to the second energy setting;
   detecting electromagnetic energy fluoresced by the portion of the thermally grown oxide in response to exposure to the second energy setting; and
   estimating a remaining life of the thermal barrier coating based on the electromagnetic energy fluoresced by the portion of the thermally grown oxide.

2. The method of claim 1, wherein the article further comprises a contaminant layer on the thermally insulative layer, and wherein determining, based on the collected spectrum of electromagnetic energy, whether the component of the thermally insulative layer is present in the portion of the article further comprises determining, based on the collected spectrum of electromagnetic energy, a presence of a component of the contaminant layer in the portion of the article.

3. The method of claim 2, wherein the portion of the article comprises a first portion of the article, wherein the article further comprises a second portion comprising the contaminant layer, and wherein the method further comprises:
   exposing the second portion to sufficient electromagnetic energy to ablate the second portion;
   collecting a spectrum of electromagnetic energy emitted by the second portion after ablation; and
   determining, based on the collected spectrum of electromagnetic energy, whether the component of the thermally insulative layer is present in the second portion.

4. The method of claim 1, wherein outputting electromagnetic energy at the first energy setting from a laser comprises outputting electromagnetic energy at a first pulse length, and wherein outputting electromagnetic energy at the second energy setting from the laser comprises outputting electromagnetic energy at a second pulse length, and wherein the second pulse length is greater than the first pulse length.

5. The method of claim 1, wherein the portion of the thermally insulative layer is located substantially over the portion of the thermally grown oxide in a direction oriented substantially normal to a surface of the substrate.

6. The method of claim 1, wherein estimating the remaining life of the thermal barrier coating based on the electromagnetic energy fluoresced by the portion of the thermally grown oxide comprises relating a frequency shift of a peak of the electromagnetic energy to a residual stress in the thermally grown oxide and relating the residual stress in the thermally grown oxide to the remaining life of the thermal barrier coating.

7. The method of claim 1, wherein estimating the remaining life of the thermal barrier coating based on the electromagnetic energy fluoresced by the portion of the thermally grown oxide comprises relating at least one of full width of an R1 or R2 peak at half maximum of the R1 or R2 peak, a spacing between the R1 peak and the R2 peak, a Gaussian/Lorensian ratio of a peak fit, a ratio of bimodal to unimodal spectra collected, or a standard deviation of a stress for multiple measurements to the remaining life of the thermal barrier coating.

8. A system comprising: an energy source configured to output electromagnetic energy at a first energy setting to ablate a portion of a thermal barrier coating present on an article and at a second energy setting to induce fluorescence in a thermally grown oxide layer on the article, wherein the article comprising a substrate, a thermal barrier coating comprising a thermally grown oxide on the substrate, and a thermally insulative layer on the thermally grown oxide; a spectrometer configured to receive emitted electromagnetic energy emitted by the portion of the thermal barrier coating and fluoresced electromagnetic energy fluoresced by the thermally grown oxide layer; and a control unit configured to control operation of the energy source and estimate a remaining life of the thermal barrier coating based on the fluoresced electromagnetic energy.

9. The system of claim 8, wherein the article further comprises a contaminant layer on the thermal barrier coating, wherein the energy source is configured to output electromagnetic energy at the first energy setting to ablate a portion of the thermal barrier coating and the contaminant layer, and wherein the control unit is configured to determine, based on the emitted electromagnetic energy, a presence of a component of the contaminant layer in the portion of the article.

10. The system of claim 9, wherein the portion of the article comprises a first portion of the article, wherein the article further comprises a second portion comprising the contaminant layer, and wherein the control unit is further configured to:
cause the energy source to output electromagnetic energy at the first energy setting to ablate the second portion; and
determine, based on emitted electromagnetic energy emitted by the second portion, whether the component of the TBC is present in the second portion.

11. The system of claim 8, wherein the spectrometer comprises a first spectrometer and a second spectrometer, wherein the first spectrometer is configured to receive emitted electromagnetic energy emitted by the ablated portion of the thermal barrier coating, and wherein the second spectrometer is configured to receive fluoresced electromagnetic energy fluoresced by the thermally grown oxide layer.

12. The system of claim 8, wherein the control unit is configured to estimate the remaining life of the thermal barrier coating based on the fluoresced electromagnetic energy by relating a frequency shift of a peak of the electromagnetic energy to a residual stress in the thermally grown oxide and relating the residual stress in the thermally grown oxide to the remaining life of the thermal barrier coating.

13. The system of claim 8, wherein the control unit is configured to estimate the remaining life of the thermal barrier coating based on the fluoresced electromagnetic energy by relating at least one of full width of an R1 or R2 peak at half maximum of the R1 or R2 peak, a spacing between the R1 peak and the R2 peak, a Gaussian/Lorensian ration of a peak fit, a ratio of bimodal to unimodal spectra collected, or a standard deviation of a stress for multiple measurements to the remaining life of the thermal barrier coating.

14. A non-transitory computer-readable medium comprising instructions that cause a processor to: control an energy source to output electromagnetic energy at a first energy setting to expose to the first energy setting a portion of an article comprising a substrate, a thermal barrier coating comprising a thermally grown oxide on the substrate, and a thermally insulative layer on the thermally grown oxide to ablate the portion of the article, wherein the portion of the article comprises a portion of the thermally insulative layer; collect a spectrum of electromagnetic energy emitted by the portion of the article after ablation; determine, based on the collected spectrum of electromagnetic energy, that a component of the thermally insulative layer is present in the portion of the article; control the energy source to output electromagnetic energy at a second energy setting to expose a portion of the thermally grown oxide to the second energy setting, wherein the second energy setting is different than the first energy setting; detect electromagnetic energy fluoresced by the portion of the thermally grown oxide in response to exposure to the second energy setting; and estimate a remaining life of the thermal barrier coating based on the electromagnetic energy fluoresced by the portion of the thermally grown oxide.

15. A laser-induced breakdown spectroscopy system comprising:
an energy source;
a spectrometer; and
a control unit configured to:
collect a reference spectrum from a reference substrate;
control the energy source to expose a portion of an article to sufficient electromagnetic energy to ablate the portion of the article, wherein the article comprises a substrate and a thermal barrier coating on the substrate, wherein the thermal barrier coating comprises a thermally grown oxide on the substrate and a thermally insulative layer on the thermally grown oxide, and wherein the portion of the article comprises the thermally insulative layer;
collect a sample spectrum from the article by causing the spectrometer to detect electromagnetic energy emitted by the portion of the article after ablation;
cross-correlate the reference spectrum and the sample spectrum to determine a cross-correlation value; and
determine whether to stop ablation of the article based on the cross-correlation value.

16. The laser-induced breakdown spectroscopy system of claim 15, further comprising an energy source and a spectrometer, wherein the control unit is configured to:
control the energy source to expose a portion of the reference substrate to sufficient electromagnetic energy to ablate the portion of the reference substrate; and
collect the reference spectrum by causing the spectrometer to detect electromagnetic energy emitted by the portion of the reference substrate after ablation.

17. The laser-induced breakdown spectroscopy system of claim 15, wherein the sample spectrum comprises N sample intensities, wherein the reference spectrum comprises N reference intensities, and wherein the control unit is configured to determine the cross-correlation value according to the equation:

$$c = \frac{\sum_{i=1}^{N}(T_i - \overline{T})(R_i - \overline{R})}{s_R s_T},$$

wherein c is the cross-correlation value, $T_i$ represents individual intensity values in the sample spectrum, $R_i$ represents individual intensity values in the reference spectrum, $\overline{T}$ is a mean intensity value of the sample spectrum, $\overline{R}$ is a mean intensity value of the reference spectrum, $s_R$ is a sample standard deviation of the reference spectrum, and $S_T$ is a sample standard deviation of the sample spectrum.

18. The laser-induced breakdown spectroscopy system of claim 15, wherein the sample spectrum comprises a first sample spectrum, the portion comprises a first portion and the cross-correlation value comprises a first cross-correlation value, and wherein the control unit is configured to:
collect after a second ablation a second sample spectrum from a second portion of the article;
cross-correlate the reference spectrum and the second sample spectrum to determine a second cross-correlation value; and
store the second cross-correlation value and the first cross-correlation value in a data array comprising the cross-correlation values and associated ablation cycles.

19. The laser-induced breakdown spectroscopy system of claim 18, wherein the control unit is configured to:
fit an exponential function to the data array; and
determine whether to stop ablation of the article based on the cross-correlation value and the exponential function.

20. The laser-induced breakdown spectroscopy system of claim 19, wherein the control unit is configured to:
determine an asymptote of the exponential function;
calculate a threshold cross-correlation value by multiplying the asymptote by a fraction or percentage;
compare the second cross-correlation value to the threshold cross-correlation; and
stop ablation of the article when the second cross-correlation value is greater than the threshold cross-correlation value.

21. The laser-induced breakdown spectroscopy system of claim 19, wherein the control unit is configured to:
determine a derivative of the exponential function;
compare the derivative of the exponential function to a threshold derivative; and
stop ablation of the article when the derivative of the exponential function is less than the threshold derivative.

22. A method comprising:
collecting a reference spectrum from a reference substrate;
controlling an energy source to expose a portion of the article to sufficient electromagnetic energy to ablate the portion of the article, wherein the article comprises a substrate and a thermal barrier coating on the substrate, wherein the thermal barrier coating comprises a thermally grown oxide on the substrate and a thermally insulative layer on the thermally grown oxide, and wherein the portion of the article comprises the thermally insulative layer;
collecting a sample spectrum from the article by causing a spectrometer to detect electromagnetic energy emitted by the portion of the article after ablation;
cross-correlating the reference spectrum and the sample spectrum to determine a cross-correlation value; and
determining whether to stop ablation of the article based on the cross-correlation value.

23. The method of claim 22, wherein collecting the reference spectrum from the reference substrate comprises:
controlling an energy source to expose a portion of the reference substrate to sufficient electromagnetic energy to ablate the portion of the reference substrate; and
collecting the reference spectrum by causing a spectrometer to detect electromagnetic energy emitted by the portion of the reference substrate after ablation.

24. The method of claim 22, wherein the sample spectrum comprises N sample intensities, wherein the reference spectrum comprises N reference intensities, and wherein cross-correlating the reference spectrum and the sample spectrum to determine the cross-correlation value comprises calculating:

$$c = \frac{\sum_{i=1}^{N}(T_i - \overline{T})(R_i - \overline{R})}{s_R s_T},$$

wherein c is the cross-correlation value, $T_i$ represents individual intensity values in the sample spectrum, $R_i$ represents individual intensity values in the reference spectrum, $\overline{T}$ is a mean intensity value of the sample spectrum, $\overline{R}$ is a mean intensity value of the reference spectrum, $s_R$ is a sample standard deviation of the reference spectrum, and $S_T$ is a sample standard deviation of the sample spectrum.

25. The method of claim 22, wherein the sample spectrum comprises a first sample spectrum, the portion comprises a first portion and the cross-correlation value comprises a first cross-correlation value, further comprising:
collecting after a second ablation a second sample spectrum from a second portion of the article;
cross-correlating the reference spectrum and the second sample spectrum to determine a second cross-correlation value; and
storing the second cross-correlation value and the first cross-correlation value in a data array comprising the cross-correlation values and associated ablation cycles.

26. The method of claim 25, further comprising:
fitting an exponential function to the data array, and
wherein determining whether to stop ablation of the article based on the cross-correlation value comprises determining whether to stop ablation of the article based on the cross-correlation value and the exponential function.

27. The method of claim 26, wherein determining whether to stop ablation of the article based on the cross-correlation value and the exponential function comprises:
determining an asymptote of the exponential function;
calculating a threshold cross-correlation value by multiplying the asymptote by a fraction or percentage; and
comparing the second cross-correlation value to the threshold cross-correlation value to determine when to stop ablation of the article.

28. The method of claim 26, wherein determining whether to stop ablation of the article based on the cross-correlation value and the exponential function comprises:
determining a derivative of the exponential function; and
comparing the derivative of the exponential function to a threshold derivative; and
stopping ablation of the article when the derivative of the exponential function is less than the threshold derivative.

29. A non-transitory computer-readable medium comprising instructions that cause a processor to: collect a reference spectrum from a reference substrate; control an energy source to expose a portion of the article to sufficient electromagnetic energy to ablate the portion of the article, wherein the article comprises a substrate and a thermal barrier coating on the substrate, wherein the thermal barrier coating comprises a thermally grown oxide on the substrate and a thermally insulative layer on the thermally grown oxide, and wherein the portion of the article comprises the thermally insulative layer; collect a sample spectrum from the article by causing a spectrometer to detect electromagnetic energy emitted by the portion of the article after ablation; cross-correlate the reference spectrum and the sample spectrum to determine a cross-correlation value; and determine whether to stop ablation of the article based on the cross-correlation value.

30. The computer-readable medium of claim 29, wherein the sample spectrum comprises N sample intensities, wherein the reference spectrum comprises N reference intensities, further comprising instructions that cause the processor to cross-correlate the reference spectrum and the sample spectrum according to the equation:

$$c = \frac{\sum_{i=1}^{N}(T_i - \overline{T})(R_i - \overline{R})}{s_R s_T},$$

wherein c is the cross-correlation value, $T_i$ represents individual intensity values in the sample spectrum, $R_i$ represents individual intensity values in the reference spectrum, $\overline{T}$ is a mean intensity value of the sample spectrum, $\overline{R}$ is a mean intensity value of the reference spectrum, $s_R$ is a sample standard deviation of the reference spectrum, and $S_T$ is a sample standard deviation of the sample spectrum.

* * * * *